United States Patent [19]

Kelsey

[11] Patent Number: 4,841,009

[45] Date of Patent: Jun. 20, 1989

[54] SUBSTANTIALLY LINEAR MONOMERIC COMPOSITION AND LIQUID CRYSTAL POLYMERIC COMPOSITIONS DERIVED THEREFROM

[75] Inventor: Donald R. Kelsey, Hillsborough, N.J.

[73] Assignee: Amoco Corporation, Chicago, Ill.

[21] Appl. No.: 752,010

[22] Filed: Jul. 5, 1985

Related U.S. Application Data

[63] Continuation of Ser. No. 454,179, Dec. 28, 1982, abandoned.

[51] Int. Cl.$^4$ .............. C07C 69/017; C07C 39/21; C07C 103/133; C07C 87/80; C07D 209/56; C07D 277/70; C08G 73/16; C08G 73/08; C08G 65/40; C08G 63/62

[52] U.S. Cl. .................. 528/75; 252/299.5; 252/299.6; 252/299.7; 528/167; 528/170; 528/174; 528/192; 528/196; 528/203; 528/204; 528/205; 528/219; 528/289; 528/291; 350/350 R; 350/352; 534/845; 534/850; 534/853; 546/257; 548/151; 548/433; 558/410; 560/141; 564/148; 564/155; 564/274; 564/305; 564/310; 564/311; 564/443; 568/718

[58] Field of Search ............ 568/718; 546/257; 548/151, 433; 558/410; 560/141; 564/155, 224, 443, 305, 148, 155, 274, 305, 568-718, 148, 310, 311; 528/75, 192, 196, 203, 204, 205, 219, 291, 289, 170, 345, 167, 174, 211; 350/350 R, 352; 252/299.5, 299.66, 299.7; 534/843, 850, 853

[56] References Cited

U.S. PATENT DOCUMENTS

| | | | |
|---|---|---|---|
| 2,632,004 | 3/1953 | Minsk et al. | 534/843 |
| 3,254,562 | 6/1966 | Blout et al. | 88/65 |
| 3,549,358 | 12/1970 | Clecak et al. | 534/689 |
| 3,656,909 | 4/1972 | Dixon et al. | 23/253 TP |
| 3,801,528 | 4/1974 | Morgan | 528/345 |
| 3,947,375 | 3/1976 | Gray et al. | 252/299 |
| 3,970,579 | 7/1976 | Taylor | 252/299 |
| 3,988,054 | 10/1976 | Yaguchi et al. | 350/160 LC |
| 3,991,014 | 11/1976 | Kleinschuster | 260/47 C |
| 3,991,016 | 11/1976 | Morgan | 260/47 CZ |
| 4,116,861 | 9/1978 | Aftergut et al. | 534/689 |
| 4,118,372 | 10/1978 | Schaefgen | 528/192 |
| 4,128,496 | 12/1978 | Cole et al. | 534/689 |
| 4,137,193 | 1/1979 | Osman et al. | 252/299 |
| 4,293,435 | 10/1981 | Portugall et al. | 252/299.01 |
| 4,325,871 | 4/1982 | Sasaki et al. | 534/689 |
| 4,327,020 | 4/1982 | Sasaki et al. | 534/689 |
| 4,384,107 | 5/1983 | Rogers et al. | 528/192 |
| 4,394,194 | 7/1983 | Gaudiana et al. | 528/192 |
| 4,412,059 | 10/1983 | Krigbaum et al. | 528/192 |
| 4,461,888 | 7/1984 | Rogers et al. | 528/205 |
| 4,520,189 | 5/1985 | Rogers et al. | 528/205 |
| 4,521,588 | 6/1985 | Rogers et al. | 528/205 |

OTHER PUBLICATIONS

Abel El-Fatah et al.: CA 83 9348r (1975).
Rizvi et al.: CA 86 82992n (1977).
Abdon et al: CA 89 163,163g (1978).
Sek, D.: CA 101 192592t (1984).
Maheshvari et al.: CA 101 110,656e (1984).
Sek, D.: CA 103 6954f (1985).
P. J. Flory and G. Ronca, Mol. Cryst. Liq. Cryst., 54, 289,311 (1979).
J. I. Jin, S. Antoun, C. Ober and R. W. Lenz, The British Polymer Journal, pp. 132–146, Dec. 1980.
W. J. Jackson, Jr. and H. F. Kuhfuss, J. Polym. Sci., Poly. Chem. Ed., 14, 2043–2058 (1976).
R. W. Lenz and J. I. Jin, Macromolecules, 14, 1405–1411 (1981).
W. Jerome Jackson, Jr., The British Polymer Journal, pp. 154–162, Dec. 1980.
Brian P. Griffin and Michael K. Cox, The British Polymer Journal, pp. 147–153, Dec. 1980.
Anselm C. Griffin and Thomas R. Britt, J. Am. Chem. Soc., 103, pp. 4957–4959 (1981).

*Primary Examiner*—Veronica P. Hoke
*Attorney, Agent, or Firm*—Donald M. Papuga; William H. Magidson; Ralph C. Medhurst

[57] ABSTRACT

Described herein are novel substantially linear monomeric compositions which can be polymerized with one or more difunctional monomers to give novel polymeric compositions having liquid crystal properties. This invention is also directed to a process for preparation of the novel substantially linear monomeric compositions.

46 Claims, No Drawings

SUBSTANTIALLY LINEAR MONOMERIC COMPOSITION AND LIQUID CRYSTAL POLYMERIC COMPOSITIONS DERIVED THEREFROM

This application is a continuation of prior U.S. application Ser. No. 454,179, filed Dec. 28, 1982, now abandoned.

BRIEF SUMMARY OF THE INVENTION

1. Technical Field

This invention is directed in general to novel substantially linear monomeric compositions which can be polymerized with one or more difunctional monomers to give novel polymeric compositions having liquid crystal properties. This invention is also directed to a process for preparation of the novel substantially linear monomeric compositions.

2. Background Art

Liquid crystal materials are well known in the art. These materials generally consist of monomeric and polymeric compositions whose degree of molecular order either in solution (lyotropic) or in melt (thermotropic) is intermediate between the molecular order of isotropic liquids and the molecular order of solid crystals. The thermotropic liquid crystal materials are generally classified as nematic, smectic and cholesteric depending on the degree and type of molecular orientation. Materials in which the monomer or polymer units exhibit an orientation in the liquid crystal state are generally classified as nematic liquid crystals. If the monomer or polymer units have both orientation and stratification or arrangement in layers in the liquid crystal state, the materials are generally classified as smectic liquid crystals. Cholesteric liquid crystals generally have orientation of a Considerable research effort in recent years has been directed toward the preparation of monomeric and polymeric compositions having liquid crystal properties. The unique ordering properties of these monomeric and polymeric compositions into liquid crystal materials has resulted in the preparation of high modulus, high tensile strength and high impact resistant fibers, for example, the anisotropic polymeric composition of E. I. duPont de Nemours and Company designated as Kevlar® can be formed into high strength fibers by spinning from a preoriented liquid crystalline solution. See Chemical Week, Nov. 24, 1976, p. 81ff; P. W. Morgan, Amer. Chem Soc., Polymer Preprints, 17 (1), 47 (1976); S. L. Kwolek, P. W. Morgan, J. R. Schaefgen and L. W. Gulrich, ibid., 53 (1976), T. I. Blair, P. W. Morgan and F. L. Killian, ibid., 59 (1976); M. Panar and L. F. Beste, ibid., 65 (1976); J. W. Ballon, ibid., 75 (1976); U.S. Pat. No. 3,991,014 and U.S. Pat. No. 3,991,016. Eastman Kodak Company has reported experimental "self-reinforcing" polymeric compositions commercially designated as X7G and X7H which show anisotropic behavior in bulk, injected-molded samples. See W. J. Jackson, Jr. and H. F. Kuhfuss, J. Polym. Sci., Poly. Chem. Ed., 14, 2043 (1976).

Other representative publications which discuss monomeric and polymeric compositions having liquid crystal properties include: J. I. Jin, S. Antoun, C. Ober and R. W. Lenz, The British Polymer Journal, Thermotropic Liquid Crystalline Polyesters with Rigid or Flexible Spacer Groups, pp. 132–146, December 1980; R. W. Lenz and J. I. Jin, Macromolecules, Liquid Crystal Polymers. 3. Thermotropic Rigid Aromatic Copolyesters with Bisphenol Spacers, 14, 1405–1411 (1981); W. Jerome Jackson, Jr., The British Polymer Journal, Liquid Crystal Polymers. IV. Liquid Crystalline Aromatic Polyesters, pp. 154–162, December 1980; Brian P. Griffin and Michael K. Cox, The British Polymer Journal, Thermotropic Polyesters with Non-Linear Links, pp. 147–153, December 1980; and Anselm C. Griffin and Thomas R. Britt, J. Am. Chem. Soc., Effect of Molecular Structure on Mesomorphism. Flexible-Center Siamese-Twin Liquid Crystalline Diesters - A "Prepolymer" Model, 103, 4957–4959 (1981). See also U.S. Pat. Nos. 3,947,375; 4,293,435; 3,656,909; 4,137,193; 3,988,054; and 3,970,579.

According to the present invention there is provided novel substantially linear monomeric compositions which can be polymerized with one or more difunctional monomers to give novel polymeric compositions having liquid crystal properties.

DISCLOSURE OF THE INVENTION

The present invention is directed to novel substantially linear monomeric compositions of the formula

wherein $R^1$ and $R^4$ are individually a substituted or unsubstituted aromatic or heteroaromatic group having from 5 to about 20 carbon atoms, $R^2$ is a substituted or unsubstituted aromatic, heteroaromatic or cycloaliphatic group having from 5 to about 20 carbon atoms, $R^3$ is a substituted or unsubstituted divalent group of the formula

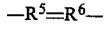

wherein $R^5$ and $R^6$ are individually carbon, nitrogen, phosphorus or silicon, $E^1$ and $E^2$ are individually a hydroxyl radical, an amino radical or an acyl radical having the formula

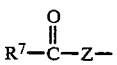

wherein $R^7$ is hydrogen, hydroxyl, halogen or a substituted or unsubstituted alkyl, aryl or arylalkyl group having from 1 to about 20 carbon atoms and Z is oxygen or nitrogen, and wherein m has a value of at least 2 and n has a value of at least 1 such that the aspect ratio of the composition is from about 3.5 to about 7.0 and, when m and/or n are values of 2 or greater, $R^2$ and/or $R^3$ individually can be the same or different groups, and the $R^2$ and $R^3$ group(s) can be arranged in any order provided two or more $R^3$ groups are not directly connected to each other with a chemical bond.

The present invention is also directed to a process for preparing a substantially linear monomeric composition which comprises:

(1) preparing a reaction mixture comprising at least one difunctional reactant and, in at least stoichiometric amounts, at least one monofunctional reactant;

(2) reacting said reactants for a time and at a temperature sufficient to form a product mixture comprising a substantially linear monomeric composition of the formula:

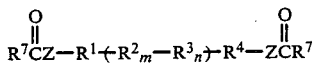

wherein
$R^1$ and $R^4$ are individually a substituted or unsubstituted aromatic or heteroaromatic group having from 5 to about 20 carbon atoms, $R^2$ is a substituted or unsubstituted aromatic, heteroaromatic or cycloaliphatic group having from 5 to about 20 carbon atoms, $R^3$ is a substituted or unsubstituted divalent group of the formula

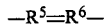

wherein
$R^5$ and $R^6$ are individually carbon, nitrogen, phosphorus or silicon, $R^7$ is hydrogen, hydroxyl, halogen or a substituted or unsubstituted alkyl, aryl or arylalkyl group having from 1 to about 20 carbon atoms and Z is oxygen or nitrogen, and
wherein
m has a value of at least 2 and n has a value of at least 1 such that the aspect ratio of the composition is from about 3.5 to about 7.0 and, when m and/or n are values of 2 or greater, $R^2$ and/or $R^3$ individually can be the same or different groups, and the $R^2$ and $R^3$ group(s) can be arranged in any order provided two or more $R^3$ groups are not directly connected to each other with a chemical bond; and (3) optionally reacting the product mixture comprising the substantially linear monomeric composition prepared in (2) with a protic solvent in the presence of an acidic or basic catalyst for a time and at a temperature sufficient to form a product mixture comprising a substantially linear monomeric composition of the formula:

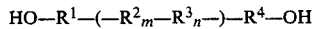

or the diamino analog thereof, wherein $R^1$, $R^2$, $R^3$, $R^4$, m and n are as defined hereinbefore.

The present invention is further directed to a process for preparing a polymeric composition comprising polymerizing one or more difunctional monomers with a substantially linear monomeric composition of the formula

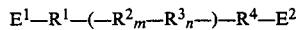

wherein
$R^1$ and $R^4$ are individually a substituted or unsubstituted aromatic or heteroaromatic group having from 5 to about 20 carbon atoms, $R^2$ is a substituted or unsubstituted aromatic, heteroaromatic or cycloaliphatic group having from 5 to about 20 carbon atoms, $R^3$ is a substituted or unsubstituted divalent group of the formula

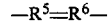

wherein
$R^5$ and $R^6$ are individually carbon, nitrogen, phosphorus, or silicon, $E^1$ and $E^2$ are individually a hydroxyl radical, an amino radical or an acyl radical having the formula

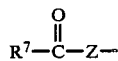

wherein
$R^7$ is hydrogen, hydroxyl, halogen or a substituted or unsubstituted alkyl, aryl or arylalkyl group having from 1 to about 20 carbon atoms and Z is oyxgen or nitrogen, and
wherein
m has a value of at least 2 and n has a value of at least 1 such that the aspect ratio of the composition is from about 3.5 to about 7.0 and,
when m and/or n are values of 2 or greater,
$R^2$ and/or $R^3$ individually can be the same or different groups, and the $R^2$ and $R^3$ group(s) can be arranged in any order provided two or more $R^3$ groups are not directly connected to each other with a chemical bond, in the presence of an aprotic solvent at a temperature of from about ambient to about 400° C. for a period of from about 1 hour to about 96 hours.

The present invention is yet further directed to polymeric compositions prepared in accordance with the process described hereinabove including polymeric compositions having liquid crystal properties.

DETAILED DESCRIPTION

The novel substantially linear monomeric compositions of this invention have the general formula

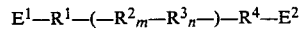

wherein $E^1$, $R^1$, $R^2$, $R^3$, $R^4$, $E^2$, m and n are described above. The preferred substantially linear monomeric compositions of this invention are aromatic bisphenols of the formula

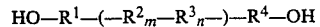

and the diamino analogs thereof, wherein $R^1$, $R^2$, $R^3$, $R^4$, m and n are as described above. Also preferred are ester derivatives of the substantially linear monomeric compositions which have the general formula

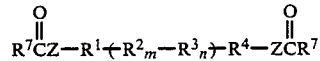

wherein $R^1$, $R^2$, $R^3$, $R^4$, $R^7$, Z, m and m are as described above. $E^1$ and $E^2$ can individually be a hydroxyl radical, an amino radical or an acyl radical and thus it is possible to have both mono-ester derivatives and diester derivatives and also the nitrogen analogs such as the mono-amide derivatives and the diamide derivatives. $R^7$ can be hydrogen, hydroxyl, halogen or a substituted or unsubstituted alkyl, aryl or arylalkyl group having from 1 to about 20 carbon atoms, preferably from 1 to about 12 carbon atoms. $R^7$ is most preferably methyl such that the acyl radical is an acetate radical. Z can be oxygen or nitrogen.

$R^1$ and $R^4$ can individually be a substituted or unsubstituted aromatic or heteroaromatic group having from 5 to about 20 carbon atoms, preferably from 5 to about 15 carbon atoms. $R^1$ and $R^4$ can be the same or different substituent in a single monomeric composition. $R^1$ and R⁴ are most preferably a para-phenylene diradical group, a 4,4'-biphenylene diradical group and the like. Para attachment is preferred to form the rigid substantially linear monomeric compositions of this invention.

R² can be a substituted or unsubstituted aromatic, heteroaromatic or cycloaliphatic group having from 5 to about 20 carbon atoms, preferably from 5 to about 15 carbon atoms. R² is most preferably a para-phenylene diradical group, a 4,4'-biphenylene diradical group, a trans-1,4-cyclohexadiyl diradical group, a pyromellitic diimide diradical group of the formula

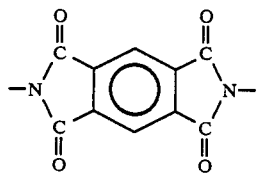

and the like. Again, para attachment is preferred to form the rigid substantially linear monomeric compositions of this invention. The value of m is at least 2, preferably from 2 to about 4. The substantially linear monomeric compositions of this invention contain a minimum of four ring structures, either substituted or unsubstituted aromatic or heteroaromatic group(s) and possibly cycloaliphatic group(s).

R³ can be a substituted or unsubstituted divalent group of the formula

wherein R⁵ and R⁶ are individually carbon, nitrogen, phosphorus or silicon, and thus it is possible to have among others substituted and unsubstituted divalent groups of the formulas

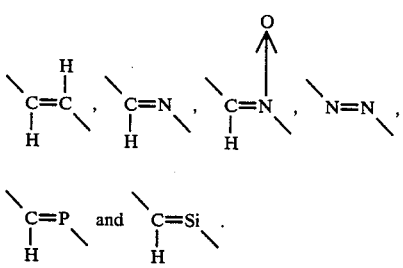

R⁵ and R⁶ are most preferably carbon and/or nitrogen. In order to achieve an aspect ratio of from about 3.5 to about 7.0 as required for the substantially linear monomeric compositions of this invention, it is generally necessary that the divalent groups have trans configurations. Cis configurations generally give monomeric compositions having aspect ratios less than 3.5 and not having the rigid rod-shaped structure. The value of n is at least one, preferably from 1 to about 4. However, it is necessary that when 2 or more R³ groups are present in the monomeric compositions, the R³ groups should not be directly connected to each other with a chemical bond. Monomeric compositions having two or more R³ groups directly connected to each other with a chemical bond may introduce excessive conformational flexibility into the monomeric compositions and are therefore not preferred in this invention.

When m is a value of 2 or greater, R² can be the same or different groups. For example, when m is a value of 2, R² can consist of one para-phenylene diradical group and one 4,4'-biphenylene diradical group. R² can also consist of two para-phenylene diradical groups or two 4,4'-biphenylene diradical groups. The same is also true for R³. When n is a value of 2 or greater, R³ can be the same or different groups. For example, when n is a value of 2, R³ can consist of one divalent group of the formula

and one divalent group of the formula

R³ can also consist of two divalent groups of the formula

or two divalent groups of the formula

The R² and R³ groups can be arranged in any order in the monomeric compositions provided two or more of the R³ groups are not directly connected to each other with a chemical bond.

The aspect ratio of the substantially linear monomeric compositions of this invention is from about 3.5 to about 7.0. The aspect ratio is defined as the length of the monomeric composition divided by the width of the monomeric composition as determined in the following manner. The molecular axis of the monomeric composition is taken to be the straight line joining the oxygen or nitrogen atoms of a typical monomeric composition of the formula:

$$E^1-R^1-(-R^2{}_m-R^3{}_n-)-R^4-E^2$$

wherein $E^1$, $E^2$, $R^1$, $R^2$, $R^3$, $R^4$, m and n are as described hereinabove, the straight line passing through the nuclei of the oxygen or nitrogen atoms. After allowing for various conformations which may result from rotations about the single bonds which constitute the monomeric composition, the conformation is selected which results in the maximum distance along the molecular axis between the oxygen or nitrogen atoms which includes the van der Waals radii of the oxygen or nitrogen atoms. This maximum distance is considered the length of the monomeric composition. The molecule in the above conformation is then rotated 360 degrees about the molecular axis which, when the van der Waals radii of the various constituent atoms and groups are included, defines a volume and surface of rotation. The radius of this volume at any point on its surface is defined as the distance from that particular point to the molecular axis along a line dropped from the point normal to and intersecting the molecular axis. The maximum radius is the greatest distance so measured from the volume surface to the molecular axis. This maximum distance doubled is considered the width of the monomeric composition.

The length and width of the monomeric compositions can be measured geometrically using the appropriate bond lengths, bond angles and van der Waals radii for the constituent atoms and groups. See, for example, Tables of Interatomic Distances and Configuration in Molecules and Ions, Special Publication No. 11, The Chemical Society, Burlington House, London, 1958; and Special Publication No. 18, 1965. A particularly convenient way to measure the length and width of the monomeric compositions is to construct a three-dimensional solid model using the appropriate CPK TM space-filling atomic models commercially available from the Ealing Corporation, Cambridge, Mass. The length and width of the monomeric compositions can be determined quite accurately by measuring the appropriate distances on the constructed three-dimensional CPK TM space-filling molecular model. The aspect ratios reported for the substantially linear monomeric compositions of this invention were determined from the appropriate CPK TM space-filling molecular models of the monomeric compositions. As will be evident to one skilled in the art, slight variations in the bond lengths, bond angles and van der Waals radii used to construct the geometrical models of the particular monomeric compositions will result in slight variations in the calculation of the length and width of the monomeric composition and hence also in the aspect ratio. However, such variations will generally result in less than 0.2 units below or above the nominal aspect ratio value as measured on CPK TM atomic models.

It is believed that for aspect ratios below about 3.5, monomeric units begin to lose their rigid rod-shaped characteristics and the polymers derived therefrom often do not exhibit liquid crystal properties. Although it is known in the prior art that certain polyesters and polyamides exhibit liquid crystal properties even though the aspect ratio of the constituent monomers are nominally less than 3.5, it is also generally believed that such polymers exhibit favored rotational conformations about the backbone single bonds such that relatively long sections of the polymer chain form a substantially rigid, rod-like structure. Such rigid, rod-like conformations, however, are difficult to attain in polycarbonates and polyarylethers based on aromatic bisphenol monomers having aspect ratios less than 3.5 and, indeed, such polycarbonate and polyarylether homopolymers have not heretofore been found to exhibit liquid crystal properties. Monomeric compositions having an aspect ratio of greater than about 7.0 are substantially insoluble in common organic solvents and cannot be easily polymerized. Interestingly, in P. J. Flory and G. Ronca, Mol. Cryst. Liq. Cryst., 54, 289, 311 (1979), a theoretical analysis suggests that the critical length to width ratio, referred to therein as axial ratio, for rod-like particles must be greater than 6.4 to produce anisotropic phases in the limit of high temperature.

Illustrative of the preferred substantially linear monomeric compositions of this invention are as follows:

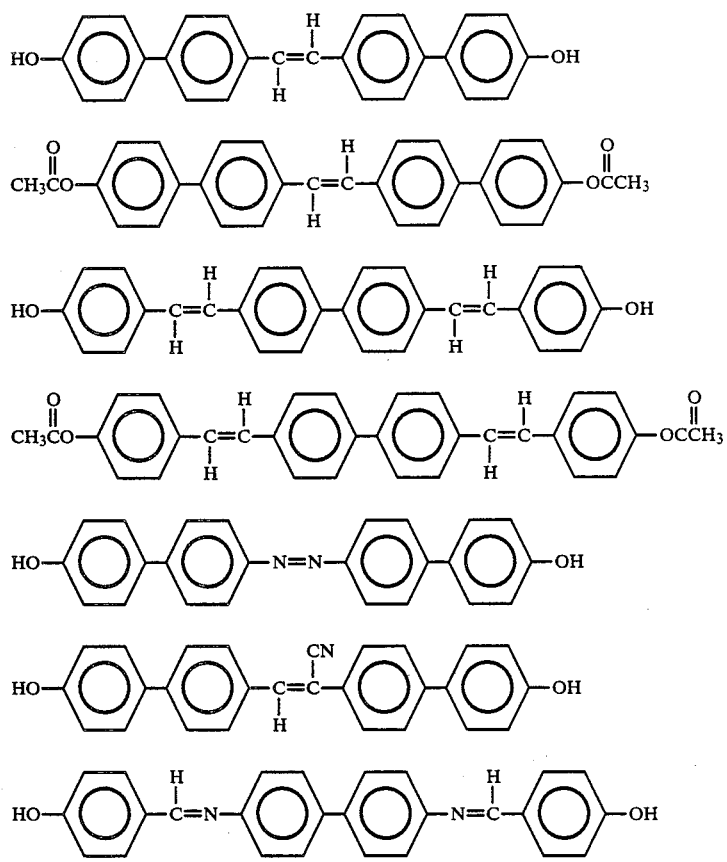

-continued
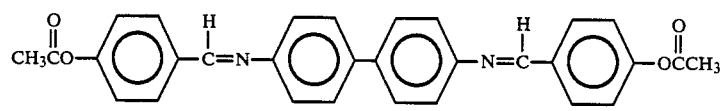
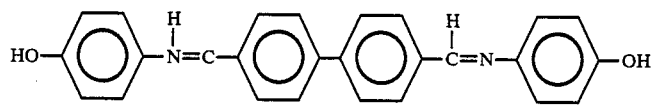
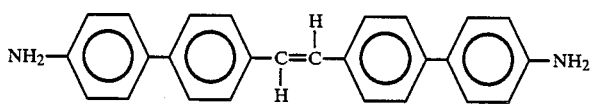
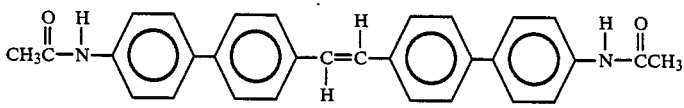
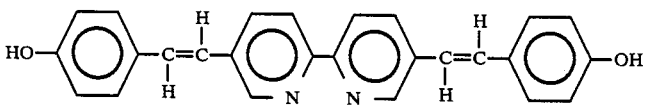
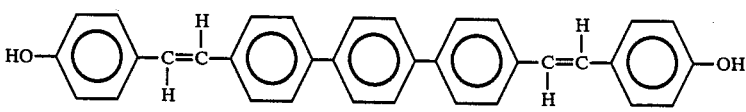
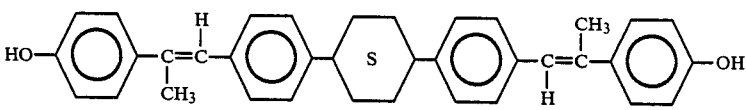
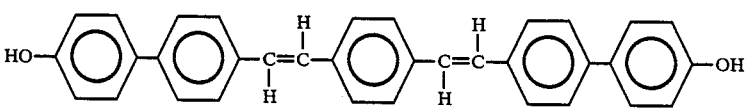
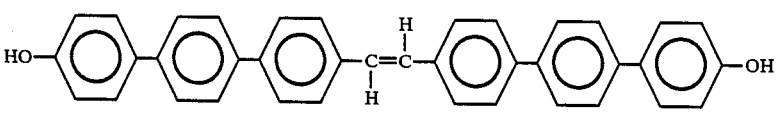

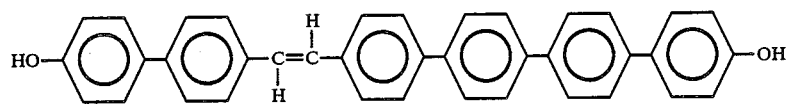
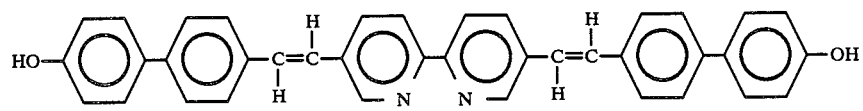
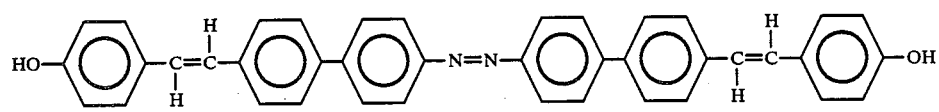
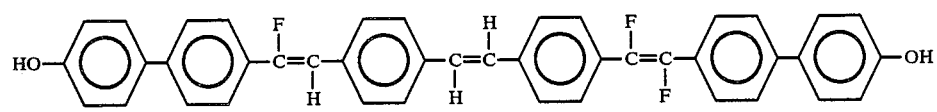
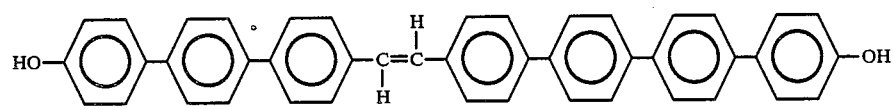
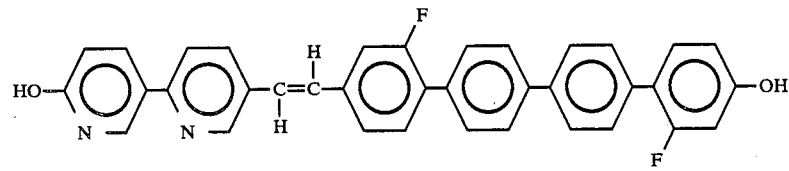
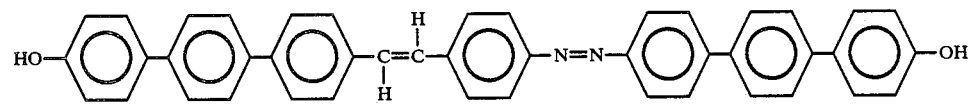
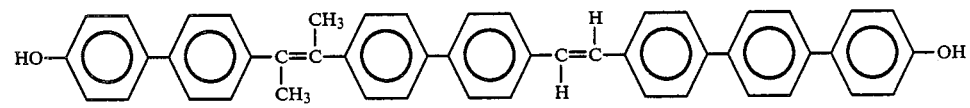
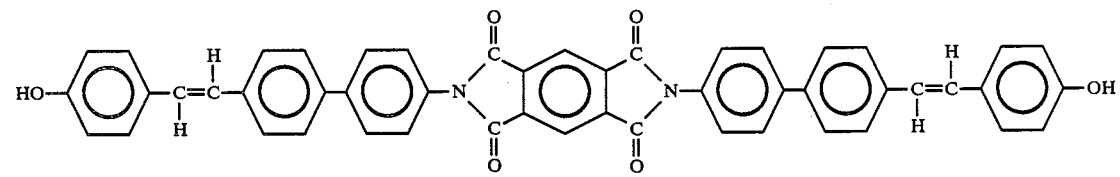
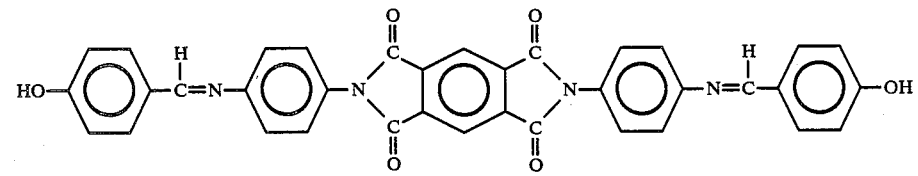
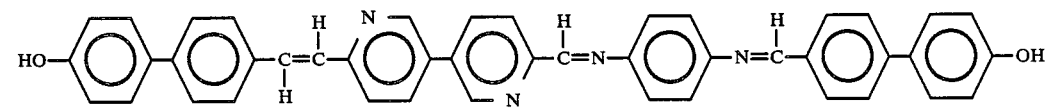
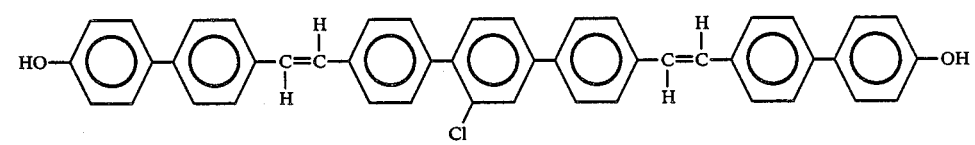

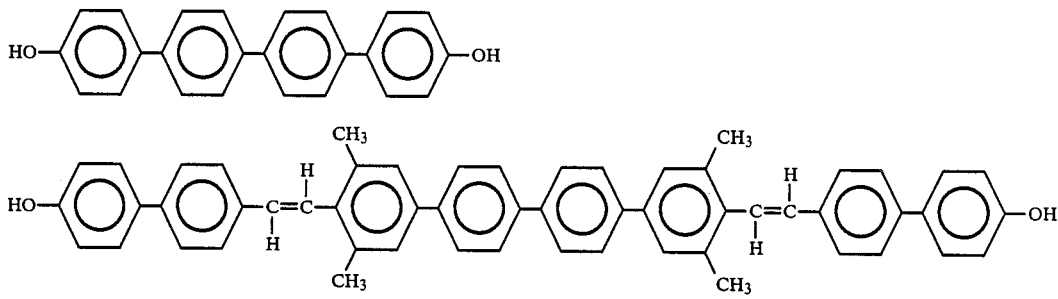

The present invention provides a process for preparing the substantially linear monomeric compositions described hereinabove. A reaction mixture is initially prepared containing at least one difunctional reactant and, in at least stoichiometric amounts, at least one monofunctional reactant. Suitable difunctional reactants include, for example, 4,4'-biphenyldialdehyde, 4,4'-dibromostilbene and the like. Suitable monofunctional reactants include, for example, the triphenylphosphine salt of para-bromomethylphenyl acetate, para-chlorophenyl acetate and the like. Any suitable difunctional and monofunctional reactants may be used provided the reactants are reacted for a time and at a temperature sufficient to form a product mixture comprising a substantially linear monomeric composition of the formula

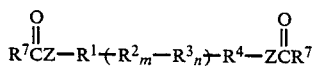

wherein $R^1$, $R^2$, $R^3$, $R^4$, $R^7$, Z, m and n are as described hereinabove. This reaction can take place at temperatures of from about 25° C. to about 350° C., preferably from about 50° C. to about 125° C. Pressure is not critical and so superatmospheric or subatmospheric pressures can be used as well as atmospheric pressure. The reaction is preferably carried out in an inert atmosphere. The reaction time can vary from one hour or less to as long as several hours, e.g., 300 hours. Suitable solvents for this reaction are generally well known in the art and may include ethanol, dimethylsulfoxide and the like. Suitable catalysts which can be used in this reaction are also generally well known in the art. The particular solvent and catalyst for use in this reaction are dependent to a degree on the specific reactants present, the solubility of the reactants and product and the reaction temperature.

The product mixture comprising the substantially linear monomeric composition above can thereafter be reacted with a protic solvent in the presence of an acidic or basic catalyst for a time and at a temperature sufficient to form a product mixture comprising a substantially linear monomeric composition of the formula

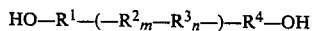

or the diamino analog thereof wherein $R^1$, $R^2$, $R^3$, $R^4$, m and n are as described hereinabove. This reaction can take place at temperatures of from about 25° C. to about 350° C., preferably from about 50° C. to about 150° C. Pressure is not critical and so superatmospheric or subatmospheric pressures can be used as well as atmospheric pressure. The reaction is preferably carried out under an inert atmosphere. The reaction time can vary from one hour or less to as long as several hours e.g., 72 hours. Suitable protic solvents for use in this process may include alcohols, preferably ethanol, and aqueous mixtures with organic solvents, such as aqueous dioxane, and the like. Suitable acidic and basic catalysts which can be used in this reaction may include such acids as the strong mineral acids, e.g., sulfuric acid, the organic acids, e.g., paratoluene sulfonic acid, and the like, and such bases as the alkali metal alkoxides, hydroxides, carbonates, and the like.

Other diluents, processing aids, additives and the like may also be present or added during the monomerization reaction provided they do not substantially interfere with the monomerization reaction either directly or indirectly. A preferred method for preparation of the substantially linear monomeric compositions of this invention is illustrated in working Examples 1 and 2 hereinbelow.

The novel polymeric compositions of this invention can be prepared by conventional polymerization techniques in which one or more difunctional monomers are reacted with the substantially linear monomeric composition of the formula

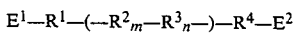

wherein $E^1$, $R^1$, $R^2$, $R^3$, $R^4$, $E^2$, m and n are as described hereinabove, in the presence of solvents and polymerization catalysts and heated to a temperature of from about ambient to about 400° C. for a period of from about 1 hour to about 96 hours. Solvents and catalysts which can be used in these conventional polymerization techniques are generally well known in the art. The particular solvent and catalyst for use in the polymerization reactions are dependent to a degree on the specific reactants present, the solubility of the reactants and product and the reaction temperature.

Suitable difunctional monomers which can be blended and polymerized with the substantially linear monomeric composition include among others the following:

(1) a difunctional monomer having the formula

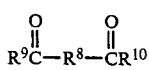

wherein $R^8$ is a substituted or unsubstituted alkyl group having from 1 to about 20 carbon atoms or a substituted or unsubstituted aromatic, heteroaromatic or cycloaliphatic group having from 5 to about 20 carbon atoms and $R^9$ and $R^{10}$ are individually halogen or $-OR^{11}$
wherein
$R^{11}$ is hydrogen or a substituted or unsubstituted alkyl, aryl or arylalkyl group having from 1 to about 20 carbon atoms, with the proviso that when $R^9$ and/or $R^{10}$ are halogen or when $R^9$ and/or $R^{10}$ are $-OR^{11}$ wherein $R^{11}$ is not hydrogen, then $E^1$ and/or $E^2$ in the substantially linear monomeric composition are a hydroxyl radical or an amino radical;

(2) a difunctional monomer having the formula $$R^{12}-\overset{O}{\underset{\|}{C}}-R^{13}$$

wherein $R^{12}$ and $R^{13}$ are individually halogen or $-OR^{14}$ in which $R^{14}$ is a substituted or unsubstituted alkyl, aryl or arylalkyl group having from 1 to about 20 carbon atoms;

(3) a difunctional monomer having the formula $$R^{15}-Ar-R^{16}$$

wherein
Ar is the residuum of a benzenoid compound having at least one electron withdrawing group in one or more of the positions ortho or para to $R^{15}$ and $R^{16}$ and
wherein
$R^{15}$ and $R^{16}$ are individually halogen, $-NO_2$, $-OSOR^{17}$ or $-OSO_2R^{18}$ in which $R^{17}$ and $R^{18}$ are a substituted or unsubstituted hydrocarbon group, preferably an aromatic group having from 1 to about 20 carbon atoms; and (4) a difunctional monomer having the formula $$O=C=N-R^{19}-N=C=O$$

wherein $R^{19}$ is a substituted or unsubstituted alkyl, aryl or arylalkyl having from 1 to about 20 carbon atoms.

The preferred difunctional monomers described in (1) above include among others aliphatic and aromatic dicarboxylic acids and the acid halides of such aliphatic and aromatic dicarboxylic acids. The preferred aliphatic dicarboxylic acids contain from 2 to about 10 carbon atoms and include, for example, adipic acid, sebacic acid and the like including adipoyl chloride and sebacoyl chloride and the like. The preferred aromatic dicarboxylic acids include terephthalic acid, isophthalic acid, any of the naphthalene dicarboxylic acids and mixtures thereof, as well as halogen and alkyl substituted homologs of these carboxylic acids, wherein the alkyl group contains from 1 to about 4 carbon atoms, and acids containing other inert substituents, such as halides, alkyl or aryl ethers, and the like. The preferred acid halides of the aromatic dicarboxylic acids include isophthaloyl chloride, terephthaloyl chloride and the like including mixtures thereof.

The polymerization of a difunctional monomer described in (1) above with the novel substantially linear monomeric composition provides novel polyester and polyamide polymeric compositions of this invention. The polyester and polyamide polymeric compositions can be prepared by any of the well known prior art polyester and polyamide forming reactions, such as the reaction of the acid chlorides of the aromatic dicarboxylic acids with dihydric phenols; the reaction of the diaryl esters of the aromatic dicarboxylic acids with dihydric phenols; or the reaction of the aromatic diacids with diester derivatives of a dihydric phenol. These processes are described in, for example, U.S. Pat. Nos. 3,317,464; 3,948,856; 3,780,148; 3,824,213; and 3,133,898. It is, of course, possible to employ two or more different dihydric phenols in the preparation of the polyester and polyamide polymeric compositions.

The preferred difunctional monomers described in (2) above include among others a carbonyl halide, a carbonate ester or a haloformate. The carbonyl halides which can be employed herein are carbonyl bromide, carbonyl chloride and mixtures hereof. Typical of the carbonate esters which may be employed herein are diphenyl carbonate, di-(halophenyl) carbonates, such as di-(chlorophenyl) carbonate or di-(bromophenyl) carbonate, etc., di-(alkylphenyl) carbonates such as di(tolyl) carbonate, di(naphthyl) carbonate, di(chloronaphthyl) carbonate, etc. or mixtures thereof. The haloformates suitable for use herein include bis-haloformate of dihydric phenols for example, bischloroformates of hydroquinone, etc. or glycols for example, bishaloformates of ethylene glycol, etc. While other carbonate precursors will be apparent to those skilled in the art, carbonyl chloride, also known as phosgene, is preferred.

The polymerization of a difunctional monomer described in (2) above with the novel substantially linear monomeric composition provides novel polycarbonate polymeric compositions of this invention. The polycarbonate polymeric compositions may be prepared by methods well known in the art by using phosgene or a haloformate and by optionally employing a molecular weight regulator, an acid acceptor and a catalyst. The molecular weight regulators which can be employed in carrying out the process include monohydric phenols, such as phenol, para-tertiary-butylphenol, para-bromophenol, primary and secondary amines, etc. Preferably, a phenol is employed as the molecular weight regulator.

A suitable acid acceptor may be either an organic or an inorganic acid acceptor. A suitable organic acid acceptor is a tertiary amine and includes materials, such as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts which are employed herein can be any of the suitable catalysts that aid the polymerization of, for example, a dihydric phenol with phosgene. Suitable catalysts include tertiary amines, such as triethylamine, tripropylamine, N,N-dimethylaniline, quaternary ammonium compounds, such as tetraethylammonium bromide, cetyl triethyl ammonium bromide, tetra-n-heptylammonium iodide, and quaternary phosphonium compounds, such as n-butyltriphenyl-phosphonium bromide and methyl-triphenyl phosphonium bromide.

The polycarbonates can be prepared in a one-phase (homogeneous solution) or a two-phase (interfacial) systems when phosgene, or a haloformate are used. Bulk reactions are possible when the diarylcarbonate precursors are used.

Aromatic polyester carbonate polymeric compositions may be prepared according to the polymerization process of this invention. For example, a polyester carbonate polymeric composition can result from the condensation of phosgene, terephthaloyl chloride, isophthaloyl chloride with a novel substantially linear monomeric composition of this invention, e.g., a dihydric phenol. It is, of course, possible to employ two or more different dihydric phenols in the preparation of the polyester carbonate polymeric composition.

The preferred difunctional monomers described in (3) above include among others any dihalobenzenoid compound or mixture of dihalobenzenoid compounds which has the two halogens bonded to benzene rings having an electron withdrawing group in at least one of the positions ortho and para to the halogen groups. The dihalobenzenoid compound can be either mononuclear where the halogens are attached to the same benzenoid ring or polynuclear where they are attached to different benzenoid rings, as long as there is an activating electron withdrawing group in the ortho or para position of the benzenoid nucleus. Any of the halogens may be the reactive halogen substituents on the benzenoid compounds. Fluorine and chlorine substituted benzenoid reactants are preferred.

A wide variety of electron withdrawing groups can be employed as the activator group in these compounds. It should be, of course, inert to the reaction, but otherwise its structure is not critical. Preferred are the strong activating groups such as the sulfone group

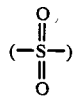

bonding two halogen substituted benzenoid nuclei as in the 4,4'-dichlorodiphenyl sulfone and 4,4'-difluorodiphenyl sulfone, although such other strong withdrawing groups hereinafter mentioned can also be used.

The preferred activating groups can be basically either of two types:

(a) monovalent groups that activate one or more halogens on the same ring such as a phenylsulfone, or alkylsulfone, cyano, trifluoromethyl, and hetero nitrogen as in pyridine; or (b) divalent group which can activate displacement of halogens on one or more different rings, such as the carbonyl group

the vinylene group

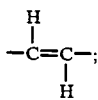

the sulfoxide group

the azo-group $-N=N-$; the saturated fluorocarbon groups $-CF_2CF_2-$; organic phosphine oxides

where R is a hydrocarbon group, and the ethylidene group

where X can be hydrogen or halogen or which can activate halogens on the same ring such as the difluorobenzoquinone, 1,4- or 1,5- or 1,8-difluoroanthraquinone. Dihalobenzenoid compounds useful in the polymerization process of this invention are further described in U.S. Pat. No. 4,175,175 and U.S. Pat. No. 4,108,837.

The preferred dihalobenzenoid compounds include, for example, 4,4'-dichlorodiphenylsulfone, 4,4'-difluorobenzophenone, 4,4'-difluorodiphenylsulfone, 4,4'-dichlorobenzophenone, and 4,4'-dichloroazobenzene. Other benzenoid compounds are preferred as well such a compound of the formula

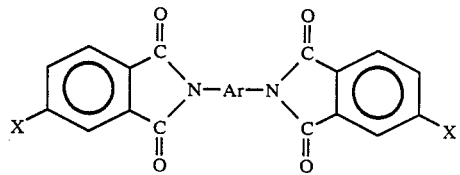

wherein Ar is an aromatic group having from 5 to about 20 carbon atoms and X is fluorine or $-NO_2$.

The polymerization of a difunctional monomer described in (3) above with the novel substantially linear monomeric composition provides novel polyether polymeric compositions of this invention. The polyether polymeric compositions can be prepared by any of the well known prior art polyether forming reactions such as the reaction of an alkali metal double salt of a dihydric phenol and dihalobenzenoid compound. These processes are described in, for example, U.S. Pat. No. 3,264,536 and U.S. Pat. No. 4,108,837. It is, of course, possible to employ two or more different dihydric phenols in the preparation of the polyester polymeric compositions. Such additional dihydric phenols can include 4,4'-biphenol, hydroquinone, 2,2-bis-(4-hydroxyphenyl) propane (bisphenol A) and the like.

The preferred difunctional monomers described in (4) above include among others diisocyanates such as ethylene diisocyanate, ethylidene diisocyanate, propylene diisocyanate, butylene diisocyanate, cyclopentylene-1,3-diisocyanate, cyclohexylene-1,4-diisocyanate, cyclohexylene-1,2-diisocyanate, 2,4-tolylene diisocyanate, 2,6-tolylene diisocyanate, 2,2'-diphenylmethane diisocyanate, 2,2'-diphenylpropane-4,4'-diisocyanate, p-phenylene diisocyanate, m-phenylene diisocyanate, xylylene diisocyanate, 2,4-naphthylene diisocyanate, 1,5-naphthylene diisocyanate, diphenyl-4,4'diisocyanate, azobenzene-4,4'-diisocyanate, diphenyl sulfone-4,4'-diisocyanate, dichlorohexamethylene diisocyanate, pentamethylene diisocyanate, 1-chlorobenzene-2,4-diisocyanate, furfurylidene diisocyanate, and the like.

The polymerization of a difunctional monomer described in (4) above with the novel substantially linear monomeric composition provides novel polyurethane polymeric compositions of this invention. The polyurethane polymeric compositions may be prepared by methods well known in the art by individually heating the substantially linear monomeric composition, an organic diisocyanate and optionally a chain extender to a temperature of from about 60° C. to about 135° C. and then the monomeric composition and chain extender are substantially simultaneously mixed with the organic diisocyanate. To increase the rate of reaction, any suitable catalyst may be used, such as tertiary amines and the like. Any suitable chain extending agent having active hydrogen containing groups reactive with isocyanate groups may be used such as diols including ethylene glycol, propylene glycol and the like. Suitable processes are described in, for example, U.S. Pat. Nos. 2,621,166, 2,729,618, 3,214,411, 2,778,810 and 3,012,992. It is, of course, possible to employ two or more different dihydric phenols in the preparation of the polyurethane polymeric compositions.

It is generally desirable to conduct the polymerization reactions in the absence of oxygen under an inert atmosphere such as argon or nitrogen. The polymerization reactions can be carried out at atmospheric, subatmospheric, or superatmospheric pressures. Reaction temperatures of up to about 250° C. are generally sufficient for the polymerization reactions although higher temperatures can be used if necessary. The temperature will depend, of course, on the solvent boiling point and the reaction pressure and will also affect the reaction rate. Obviously, the reaction solvent and the reaction temperature should be selected so as to obtain a reasonable polymerization rate and also to avoid degradation of the solvent, monomers or polymers which may cause interference with the polymerization. It is also preferable, of course, to select the reaction solvent and reaction temperature so as to maintain the growing polymer chain in solution.

Other catalysts, diluents, processings aids, additives, and the like may also be present or added during the polymerization reactions provided they do not substantially interfere with the polymerization reaction, either directly or indirectly.

The polymeric compositions of this invention are essentially linear polymers comprised of repeating units of a long rigid monomer segment and a flexible group which can be illustrated as follows:

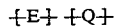

wherein E is the residuum of an aromatic monomeric composition having from 15 to about 60 carbon atoms and having an aspect ratio of from about 3.5 to about 7.0 and Q is the residuum of a difunctional monomer. More particularly, the polymeric compositions of this invention are essentially linear polymers comprised of repeating units of a long rigid monomer segment and a flexible group which can be illustrated as follows:

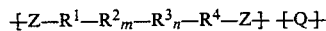

wherein $R^1$, $R^2$, $R^3$, $R^4$, Z, m and n are as described hereinabove for the monomeric composition and Q is the residuum of a difunctional monomer. As used herein, the term Q defined as being the "residuum of a difunctional monomer" refers to the residue of a monomer after removal or rearrangement of one or both functional groups therein. Q is preferably selected from the difunctional monomers (1), (2), (3) and (4) described more fully hereinabove. As used herein, the term flexible refers to groups (Q) incorporated into the polymer backbone such that the axes of the residuum of the rigid rod-shaped monomeric compositions of this invention are not forced to be parallel or colinear, especially for adjacent rigid rod-shaped residua connected by the flexible units (Q).

The concentrations of the long rigid monomer segment in the polymeric compositions of this invention can range from about 5 to about 99 weight percent. The concentration of the flexible group, i.e., difunctional monomer, in the polymeric compositions of this invention can range from about 1 to about 95 weight percent. The number average molecular weight of the polymeric compositions of this invention can range from 1000 or less to about 100,000 or greater. In general, those polymeric compositions containing the higher weight percentages of the long rigid monomeric segments will preferably display liquid crystal properties.

Illustrative of the preferred polymeric compositions of this invention include among others the following structural repeat units:

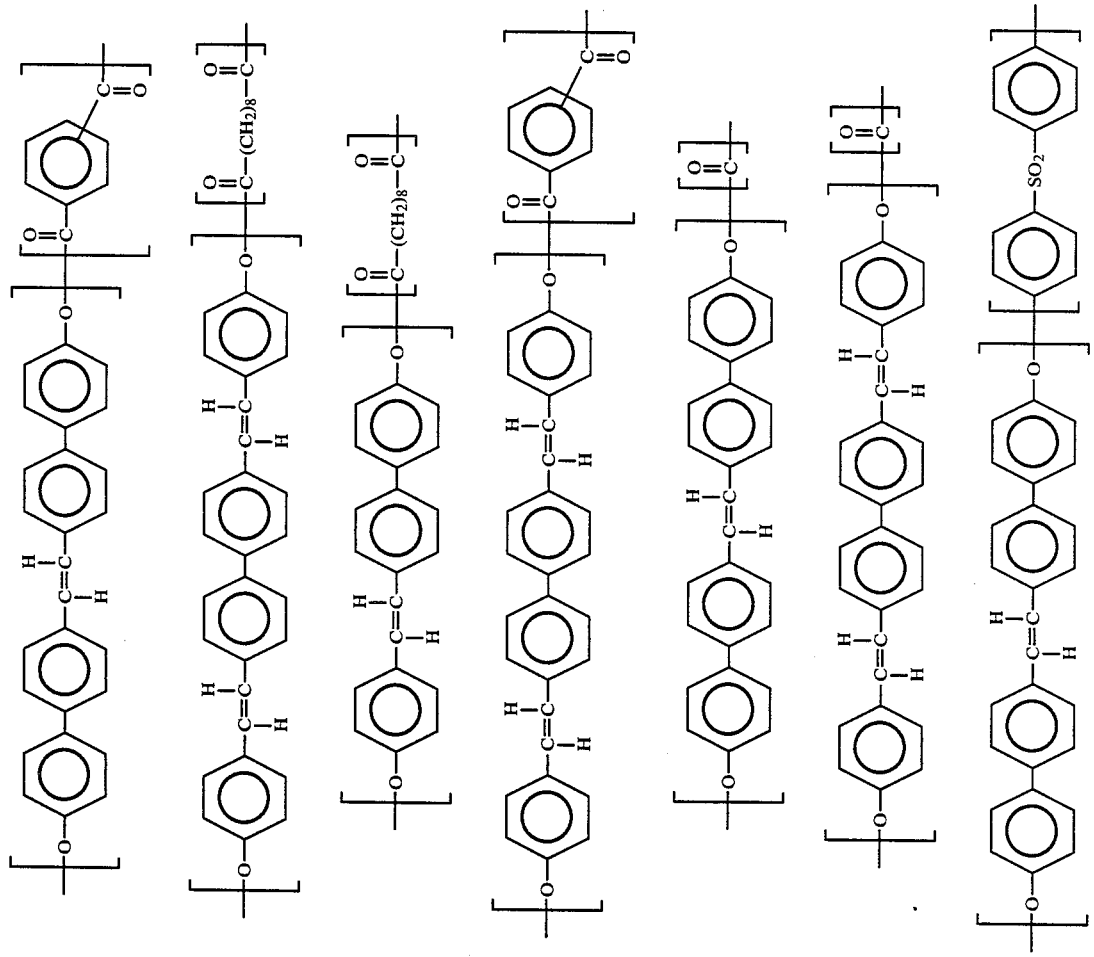

-continued
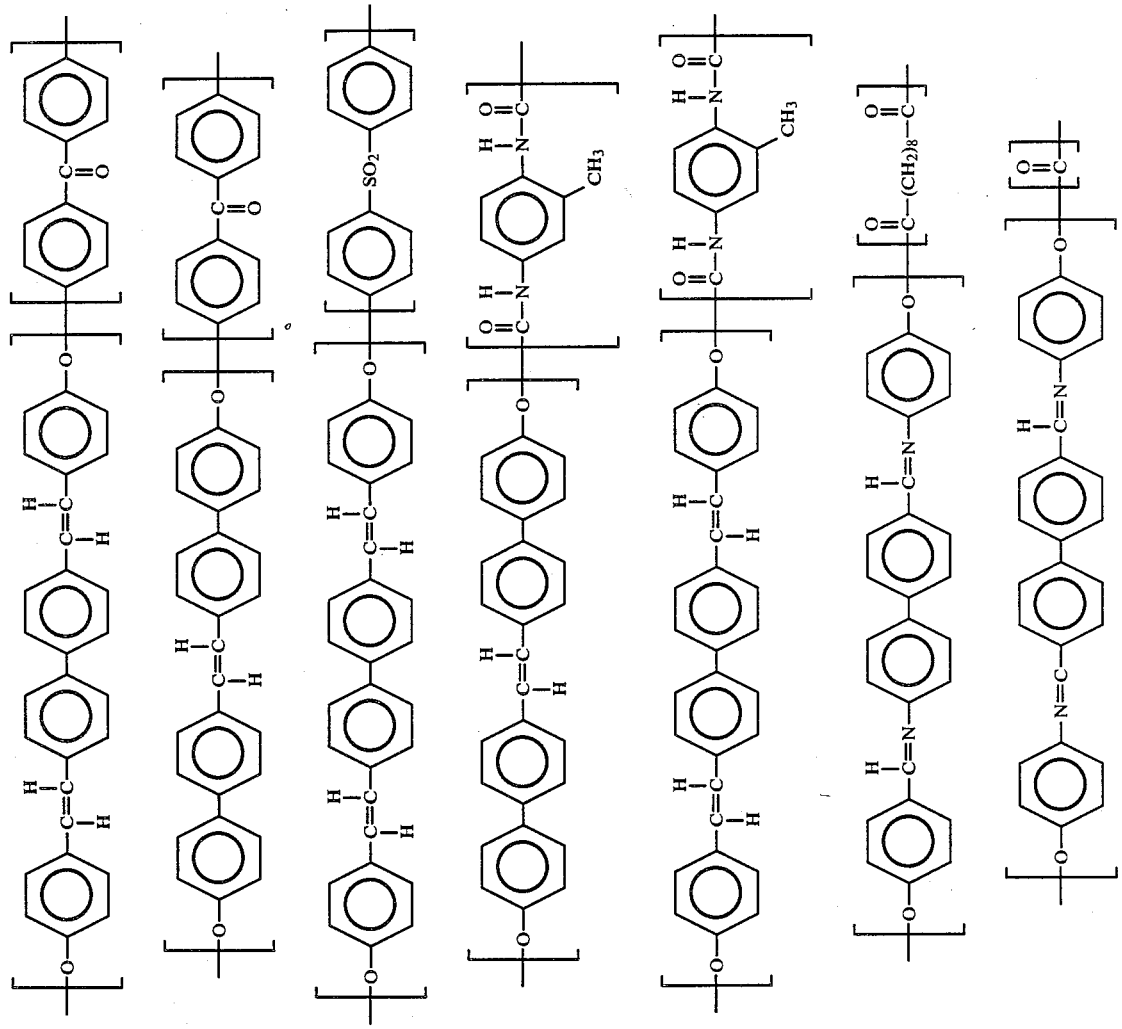

-continued
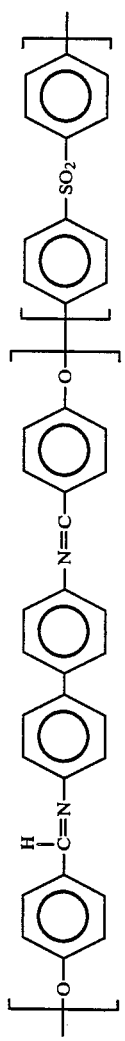 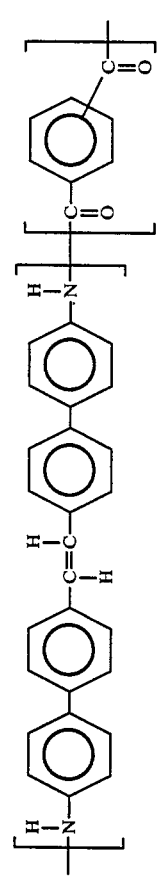 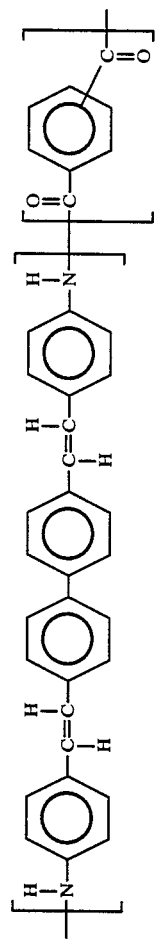 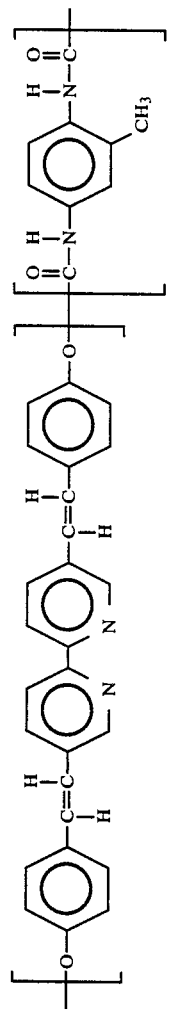 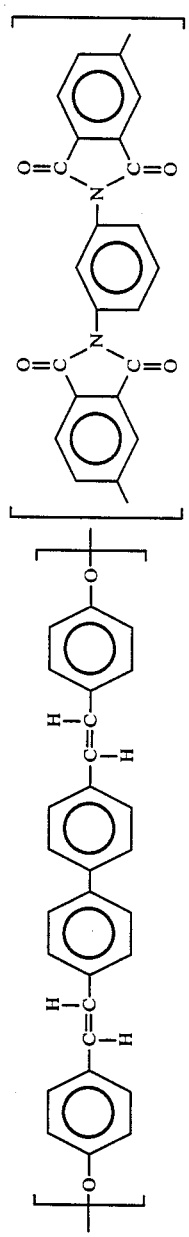

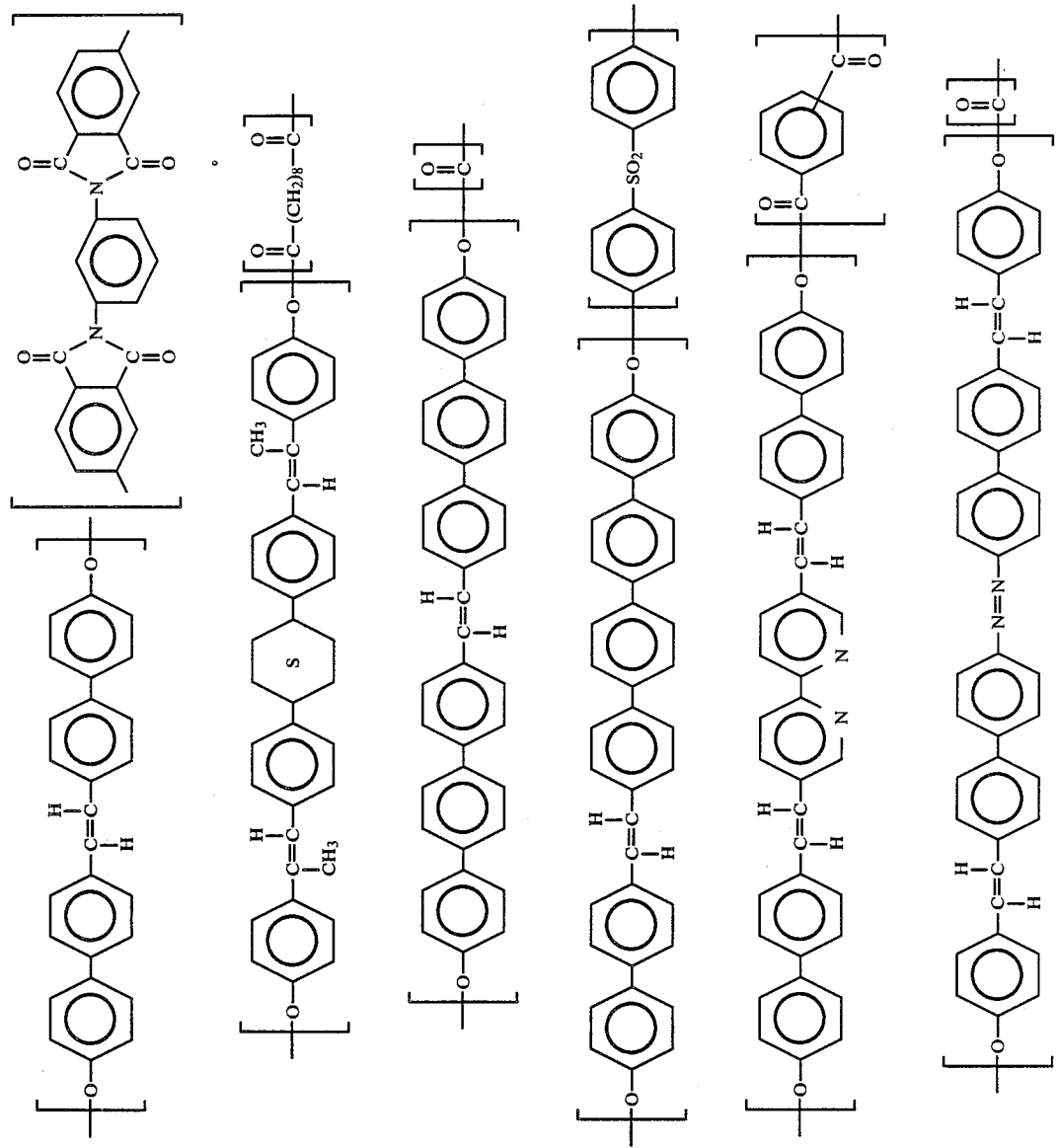

-continued
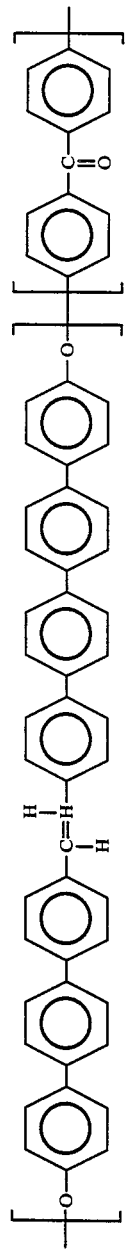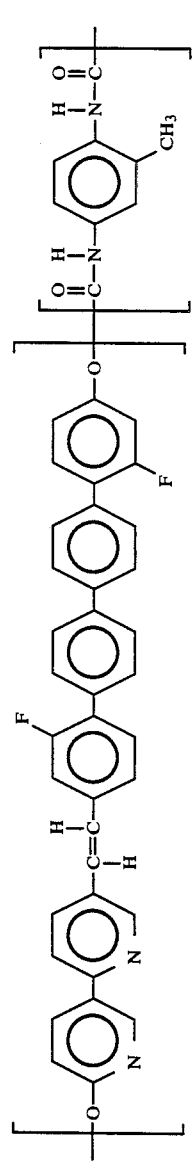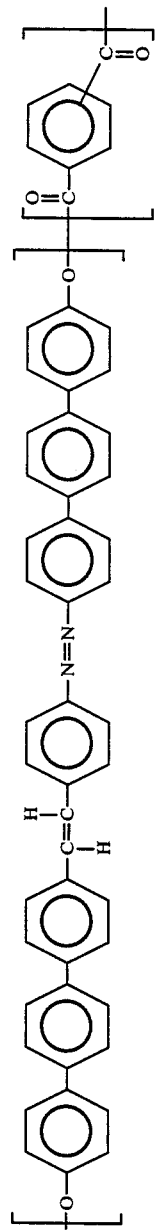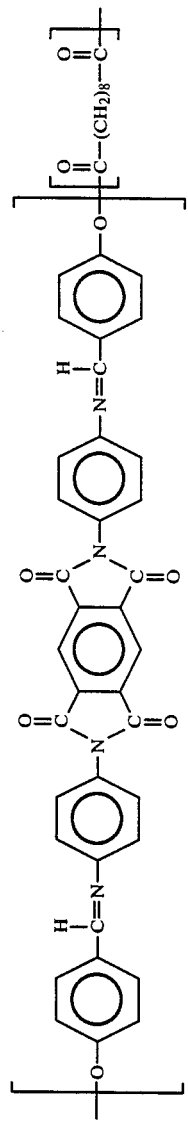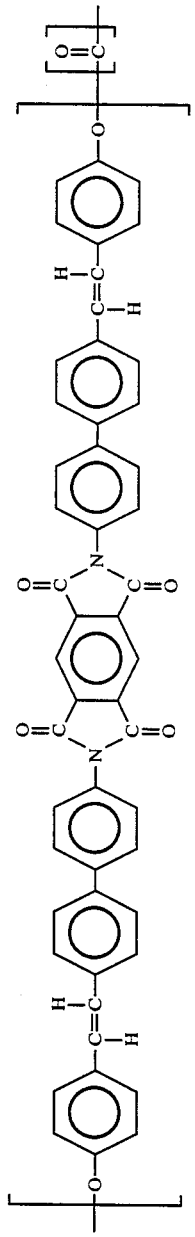

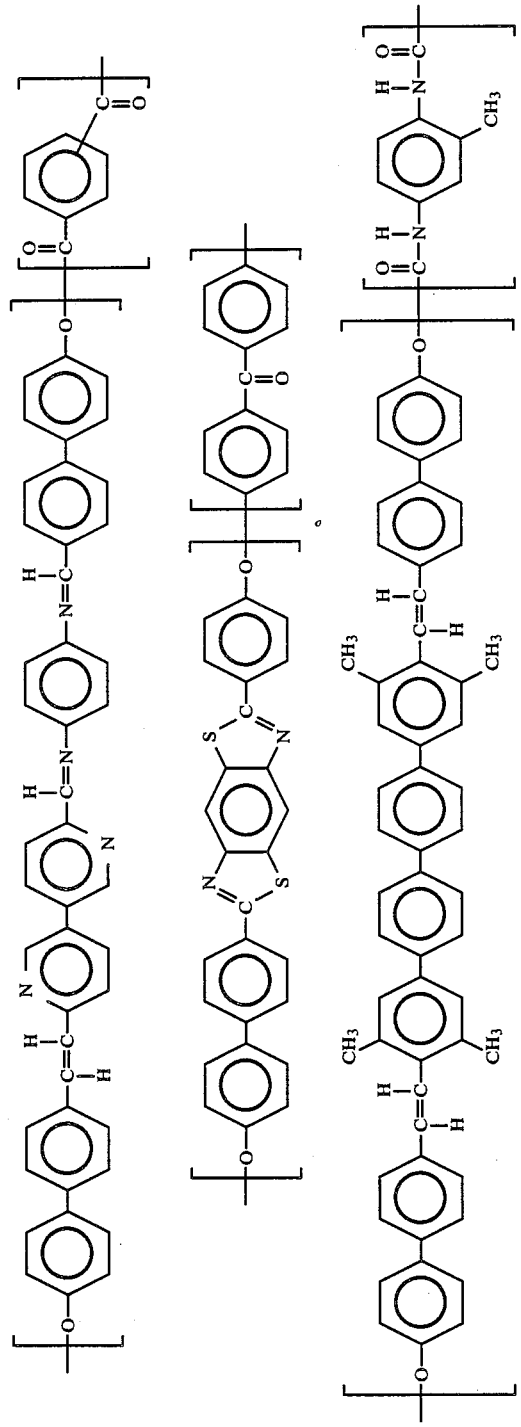

The preferred polymeric compositions of this invention exhibit liquid crystal properties. It is believed that the proportions of the long rigid monomer segment and optional bisphenol units and the flexible segment can be adjusted to give polymeric compositions having both liquid crystal character and good melt processability. Liquid crystal polymeric compositions are generally characterized by comparatively low melt viscosities and long relaxation times. Because of long relaxation times, the polymer chains in injection-molded plastics and melt-spun fibers can retain their liquid crystal orientation while the polymer is cooling, and the resulting plastics and fibers have desirably very high strength, high modulus, and high impact resistance.

The polymeric compositions of this invention can be blended with one or more other polymers to form polymeric alloy compositions. The one or more other polymers are chosen so as to attain mechanical compatability or miscibility with the novel polymeric compositions of this invention and can include, for example, polyesters, polycarbonates, polysulfones, polyimides, polyolefins, polyurethanes, polysilicones and the like. The polymeric alloy compositions may possess liquid crystal properties. When compared with individual polymeric compositions, certain polymeric alloy compositions may exhibit better processability and improved properties for certain applications.

Although this invention has been described with respect to a number of details, it is not intended that this invention should be limited thereby. The examples which follow are intended solely to illustrate the embodiments of this invention which to date have been determined and are not intended in any way to limit the scope and intent of this invention.

EXAMPLE 1

Part A

Preparation of p-Methylphenyl Acetate

Into a reaction flask equipped with a stirrer and thermometer was charged 216 grams (2.0 moles) of p-cresol, 225 grams (2.2 moles) of acetic anhydride and 500 milliliters of pyridine and the resulting reaction mixture was then heated to a temperature of 50° C.-55° C. After completion of the reaction, work-up and distillation at reduced pressure, 272 grams of p-methylphenyl acetate was obtained (91 percent of theoretical). The nuclear magnetic resonance (NMR) spectrum was consistent with the chemical structure.

Part B

Preparation of p-Bromomethylphenyl Acetate

Into a reaction flask equipped with a mechanical stirrer, thermometer and reflux apparatus was charged 75 grams (0.5 moles) of p-methylphenyl acetate prepared in Part A, 88 grams (0.5 moles) of N-bromosuccinimide, 300 milliliters of carbon tetrachloride and 1.0 gram of benzoyl peroxide. The resulting reaction mixture was carefully heated to 80° C. with a mantle, at which temperature, slight reflux ensued along with an exothermic reaction. Reflux was carefully maintained for 40 minutes and then 200 milliliters of carbon tetrachloride was gradually added to the reaction flask and the reaction mixture was then cooled to 25° C. (total time from onset of reflux was 50 minutes). The reaction mixture was filtered on a Buchner funnel and after the collected solid (succinimide) was washed four times with 100 milliliters of carbon tetrachloride, the total carbon tetrachloride solution (filtrate and washes) was stripped on a rotary evaporator. The resulting residue was distilled at reduced pressure (0.4 torr) to give a total of 92.8 grams of the desired product, whose nuclear magnetic resonance (NMR) spectrum was consistent with bromination of the aromatic methyl group: 2.13$\delta$, singlet, $CH_3O$; 4.2$\delta$, singlet, $BrCH_2$—; and 6.97, quartet, aromatic protons.

Part C

Preparation of the Triphenylphosphine Salt of p-Bromomethylphenyl Acetate

Into a reaction flask equipped with a mechanical stirrer, thermometer and reflux apparatus was added 53.2 grams (0.23 moles) of p-bromomethylphenyl acetate prepared in Part B in 550 milliliters of xylene and 67 grams of triphenylphosphine (0.26 moles, Aldrich). The contents of the reaction flask were then heated to reflux and maintained under refluxing conditions for 21 hours. After cooling, the contents in the reaction flask were filtered and the collected solids rinsed with xylene and dried under vacuum at 40° C. to give 105 grams of a product fraction (white crystals) consisting of the triphenylphosphine salt of p-bromomethylphenyl acetate (93 percent of theoretical).

Part D

Preparation of 4,4'-Biphenyl Dialdehyde

Into a two liter reaction flask equipped with a mechanical stirrer, thermometer and serum caps with needles for an argon atmosphere was charged 131 grams (2.0 moles) of zinc (cleaned and washed with acetic acid and ether and then dried) and 25.8 grams (0.25 moles) of sodium bromide and the reaction flask was then flamed and cooled under argon atmosphere. Into the reaction flask was then added 300 milliliters of dry dimethylformamide, 131 grams (0.5 moles) of triphenylphosphine and another 300 milliliters of dry dimethylformamide. The resulting reaction mixture was then purged with argon for one hour after which 6.6 grams (0.05 mole) of anhydrous nickel dichloride was added to the reaction flask. The reaction mixture was then stirred and heated with a mantle to a temperature of about 55° C. (the contents in the reaction flask began to turn red at 40° C. and then deep red at 55° C.). The heating mantle was temporarily removed and 142 grams (1.0 mole, Aldrich) of p-chlorobenzaldehyde in 100 milliliters of dry dimethylformamide (solution purged for one hour with argon) was added to the reaction flask by syringe over a 20 minute period. A mild exotherm was noted and the reaction temperature remained at 58° C.-61° C. The reaction mixture was then heated to a temperature of 70° C. and maintained at this temperature for 100 minutes (the reaction mixture turned very green after 15 minutes, and then back to red after 25 minutes and very red after 100 minutes) and thereafter cooled to 25° C. Vapor phase chromatography showed no unreacted p-chlorbenzaldehyde remaining in the reaction mixture.

The reaction mixture was isolated by dilution with 800 milliliters of ethyl acetate, filtration on a Buchner funnel to remove the zinc, further dilution of the filtrate with 1600 milliliters of ethyl acetate, washing the ethyl acetate solution several times with a total of 4800 milliliters of water, filtration of the organic solution to remove some residual solids and drying the organic solution over anhydrous sodium sulfate. The organic solution was then filtered and stripped on a rotary evaporator to give 227 grams of a residue.

The residue was slurried with 800 milliliters of toluene overnight and then filtered with a toluene wash. The collected solid was stirred with 500 milliliters of chloroform for one hour, filtered with a chloroform wash and the filtrate was stripped on a rotary evaporator. The resulting residue was slurried in 500 milliliters of isopropanol overnight, filtered and the collected solids dried in a vacuum oven to give 50.8 grams of 4,4'-biphenyl dialdehyde as determined by infrared spectroscopy and nuclear magnetic resonance (NMR) spectroscopy:9.95δ, COH; 7.92, singlet, aromatic protons.

Part E

Preparation of Diacetate Monomer

Into a two liter reaction flask equipped with an argon inlet and outlet, thermometer and magnetic stirrer was added 50 milliliters of absolute ethanol and 10.8 grams (154 millimoles) of sodium ethoxide which was washed into the flask with an additional 30 milliliters of ethanol. After stirring for 10 minutes under an argon atmosphere, 102 grams (205 millimoles) of the triphenylphosphine salt of p-bromomethylphenyl acetate (Witting salt) prepared in Part C and 100 milliliters of dimethylsulfoxide were added to the reaction flask. Additionally, 10.8 grams (51.4 millimoles) of 4,4'-biphenyldialdehyde prepared in Part D in 50 milliliters of dimethylsulfoxide was washed into the reaction flask with 100 milliliters of dimethylsulfoxide. The reaction mixture was then heated to 72° C.-75° C. and maintained at this temperature for 141 hours, during which time an additional 2.6 grams of sodium ethoxide, 650 milliliters of dimethylsulfoxide and 80 milliliters of ethanol were added in portions to the reaction mixture. Cyclohexanone (5.0 grams, 51 millimoles) was then added to the reaction mixture to consume the excess Wittig reagent. The reaction mixture was then heated for an additional 144 hours, i.e., 285 total hours, and then cooled to 20° C. to give an opalescent solution. This solution was filtered (the opalescent solution filtrate was retained for further reaction described hereinbelow) to give a solid which was slurried in 300 milliliters of a 60:40 volume ratio ethanol:water solution, filtered, the solid slurried in 200 milliliters of acetone, and filtered to give 3.77 grams of solid after drying. This solid was reacted with 20 grams (196 millimoles) of acetic anhydride in 100 milliliters of pyridine to give 4.2 grams of a product fraction containing greater than 50 weight percent, as determined by infrared spectroscopy, of a diacetate monomer having the following formula:

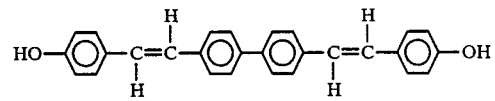

The opalescent solution filtrate from above was cooled in an ice bath and diluted with 900 milliliters of water. The resulting solution was filtered to give a solid which was then slurried in 500 milliliters of a 60:40 volume ratio ethanol:water solution for three days and filtered. The collected solid was then slurried in 400 milliliters of acetone for 24 hours and filtered.

The acetone filtrate was stripped of solvent and the solid residue collected and dried. The solid residue was reacted with 30 grams (294 millimoles) of acetic anhydride in 200 milliliters of pyridine to give 6.5 grams of the diacetate monomer having the formula described hereinabove as determined by both infrared (IR) spectroscopy and nuclear magnetic resonance (NMR) spectroscopy.

Elemental Analysis of Diacetate Monomer: 80.20% C, 5.66% H, 13.5% O. Found; 80.99% C, 5.52% H, 13.49% O calculated.

NMR Spectra (250 MHz) in dimethylsulfoxide solution confirmed the chemical and geometrical structure of the monomer. The spectra confirmed that both double bonds were the trans geometry: 2.30δ (singlet) acetate protons), aromatic protons at 7.13 (doublet), 7.63 (doublet), 7.69 (AB quartet) and trans olefinic protons at 7.26 (AB quartet vinyl coupling constant 18 Hz).

Measurement of the diacetate monomer having the formula described hereinabove on the appropriate CPK ™ space-filling molecular model gave an aspect ratio of 4.1.

Part F

Preparation of Bisphenol Monomer 2.4 grams (5.06 millimoles) of the diacetate monomer having the formula described hereinabove in Part D was stirred with 150 milliliters of absolute ethanol and a small amount (~10-30 milligrams) of sodium ethoxide in a reaction flask containing a magnetic stirrer and a drying tube at a temperature of about 80° C.-85° C. After 48 hours, the reaction mixture was cooled to ambient temperature, neutralized with 15 milliliters of a 1% hydrochloric acid solution, filtered and the solids washed with isopropanol to give 2.02 grams, as determined by nuclear magnetic resonance (NMR) spectroscopy, of a bisphenol monomer having the following formula:

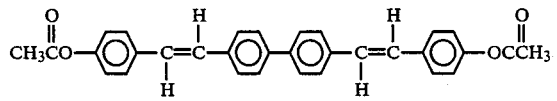

Elemental Analysis of Bisphenol Monomer: 85.41% C, 5.85% H, 8.23% O. Found; 86.13% C, 5.68% H, 8.19% O calculated.

NMR Spectra (250 MHz) in dimethylsulfoxide solution confirmed the chemical and geometrical structure of the monomer. The spectra confirmed that both double bonds are trans: aromatic protons at 6.79δ (doublet), 7.43 (doublet), 7.65 (AB quartet), trans olefinic protons at 7.10 (AB quartet coupling constant 15 Hz) and hydroxyl at 9.4 (singlet).

The bisphenol monomer having the formula described hereinabove was recrystallized from warm dimethylsulfoxide and had a melting point of about 398° C.-400° C. as determined by differential scanning calorimetry. The aspect ratio of the above bisphenol monomer was 4.1 as determined on the appropriate CPK ™ space-filling molecular model which included van der Waals radii.

EXAMPLE 2

Part A

Preparation of the Triphenylphosphine Salt of p-Bromobenzyl Bromide

Into a reaction flask equipped with a mechanical stirrer, thermometer, and reflux apparatus was added 25.4 grams (0.1 mole, Aldrich) of p-bromobenzyl bromide in 300 milliliters of xylene and 29.1 grams (0.11 moles, Aldrich of triphenylphosphine. The resulting reaction mixture was then heated and maintained under refluxing conditions for 19 hours. After cooling, the reaction mixture was filtered and the collected solids rinsed with xylene and dried under vacuum at 40° C. to give 51.4 grams (white crystals) of the triphenylphosphine salt of p-bromobenzyl bromide having a melting point of greater than 260° C.

Part B

Preparation of 4,4'-Dibromostilbene

Into a reaction flask equipped with a mechanical stirrer, condenser, drying tube and thermometer was charged 76.8 grams (0.15 moles) of the triphenylphosphine salt of p-bromobenzyl bromide prepared in Part A and 11.1 grams (0.159 mole) of sodium ethoxide in 150 milliliters of absolute ethanol. Over a ten minute period, 30.0 grams (0.162 mole, Aldrich, 99 percent) of 4-bromobenzaldehyde in 30 milliliters of absolute ethanol was added to the reaction mixture at a reaction temperature of from 30° C. to 43° C. The 4-bromobenzaldehyde was washed into the reaction flask with 10 milliliters of absolute ethanol. The reaction mixture was then heated to a temperature of 48° C. and maintained at this temperature with continuous stirring overnight. The reaction was quenched by adding 140 milliliters of distilled water to the reaction flask. A soft cream colored precipitate formed in the reaction flask which was filtered and the collected solids dried to give 15.5 grams of a crude product fraction. This crude product fraction was heated to a temperature of 122° C.-128° C. in xylene with a small crystal of iodine, cooled to ambient temperature, filtered and the collected solids were dried in a vacuum oven to give 11.2 grams of 4,4'-dibromostilbene having a melting point of from 211° -213° C.

Vapor phase chromatography showed that the crude product fraction consisted of almost a 50:50 mixture of the cis and trans isomers of 4,4'-dibromostilbene with peak retention times 1.5 minutes apart. The treatment with iodine resulted in disappearance of the shorter retention time product and enhancement of the longer retention time product. This is consistent with isomerization of the cis isomer to trans isomer. The nuclear magnetic resonance (NMR) spectrum in pyridine confirmed the chemical and geometrical (trans) structure.

Part C

Preparation of p-Chlorophenyl Acetate

Into a reaction flask equipped with a magnetic stirrer and thermometer was charged 257.2 grams (2.0 moles) of p-chlorophenol, 245 grams (2.4 moles) of acetic anhydride and 200 milliliters of pyridine and the resulting reaction mixture was then heated to a temperature of 23° C.-47° C. After completion of the reaction, work-up and distillation at reduced pressure, p-chlorophenyl acetate was obtained (93 percent of theoretical). The nuclear magnetic resonance (NMR) spectrum was consistent with the chemical structure.

Part D

Preparation of Diacetate Monomer

Into a 250 milliliter reaction flask equipped with a mechanical stirrer, thermometer and serum caps with needles for an argon atmosphere was charged 0.659 grams (5.0 millimoles) of anhydrous nickel dichloride, 13.1 grams (50 millimoles) of triphenylphosphine, 13.1 grams (200 millimoles) of cleaned and dried zinc powder and 1.872 grams (12.5 millimoles) of sodium iodide. After the reaction flask was purged with argon, 38 milliliters of dry N,N-dimethylformamide was added into the reaction flask and the reaction mixture was heated to a temperature of 40° C. to give a red-brown reaction mixture. The red-brown reaction mixture was heated to a temperature of 70° C. and an argon purged solution containing 1.271 grams (7.5 milliequivalents) of 4,4'-dibromostilbene prepared in Part B and 8.528 grams (50 milliequivalents) of p-chlorophenyl acetate prepared in Part C in 38 milliliters of dry N,N-dimethyformamide was added to the reaction flask. The reaction mixture was maintained at a temperature of 70° C.-80° C. for six hours (after three hours, the contents in the reaction flask changed from red-brown to green). The reaction was thereafter quenched with 50 milliliters of a 5 percent by weight hydrochloric acid solution, filtered and the collected solid extracted in a Soxhlet extractor with methylene chloride. The resulting methylene chloride extraction solution was washed three times (each time with 50 milliliters of water), dried over sodium sulfate, and stripped of methylene chloride to give 19.8 grams of a crude product fraction which, after trituration with ether, yielded 2.0 grams (yellow solid) of a diacetate monomer having the following formula as determined by nuclear magnetic resonance (NMR) spectroscopy:

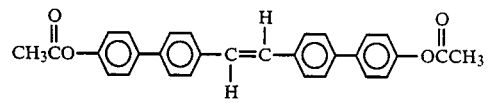

Elemental Analysis of Diacetate Monomer: 80.34% C, 5.39% H, 14.27% O. Calculated; 80.14% C, 5.51% H, 14.05% O. Found.

NMR Spectra (200 MHz) in dimethylsulfoxide solution confirmed the chemical and geometrical structure of the monomer. The spectra confirmed that the double bond is trans: 2.20 δ (singlet) acetate protons, aromatic protons at 7.21 (AB quartet), 7.71 (AB quartet) and 7.68 (singlet), and trans olefinic protons at 7.30 (singlet).

The purified diacetate monomer described above showed a sharp melting transition at 332° C. by differential scanning calorimetry. Measurement of the diacetate monomer having the formula described above on the appropriate CPK ™ space-filling molecular model gave an aspect ratio of 3.8.

Part E

Preparation of Bisphenol Monomer 0.2 grams (0.45 millimoles) of the above product fraction containing essentially the diacetate monomer having the formula described hereinabove in Part D was stirred with 60 milliliters of absolute sodium ethanol and a small amount (~10 milligrams) of sodium ethoxide in a reaction flask containing a magnetic stirrer and a drying tube at a temperature of about 50° C.-60° C. After 48 hours, the contents of the reaction flask were cooled to ambient temperature, neutralized with 5 milliliters of acetic acid, filtered, washed with ethanol, dried, recrystallized from 20 milliliters of dimethylsulfoxide, and dried in a vacuum oven to give 0.6 grams of a product fraction containing essentially, as determined by nuclear magnetic resonance (NMR) spectroscopy, a bisphenol monomer having the following formula:

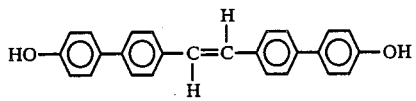

NMR Spectra (200 MH$_z$) in dimethylsulfoxide solution confirmed the chemical and geometrical structure of the monomer. The spectra confirmed that the double bond is trans, which is necessary for a rod-shaped structure: aromatic protons at 6.86 δ (AB quartet), 7.51 (AB quartet) 7.57 (AB quartet) and 7.63 (AB quartet) and trans olefinic protons at 7.23 (singlet).

The aspect ratio of the above bisphenol monomer was 3.8 as determined on the appropriate CPK TM space-filling molecular model which included van der Waals radii. The melting point of the above bisphenol monomer was 400° C.–403° C. as determined by differential scanning calorimetry.

EXAMPLE 3

Preparation of Polyester Polymeric Composition

Into a large, thickwalled pyrex test tube equipped with a magnetic stirrer and serum cap with a syringe needle for an argon atmosphere was charged 195.8 milligrams (0.5014 millimoles) of the bisphenol monomer prepared in accordance with the peocedure described in Example 1 and 101.9 milligrams (0.5019 millimoles) of isophthaloyl chloride (recrystallized from hexane). The test tube was sealed with the serum cap and the contents in the test tube were flushed with argon after which 5 milliliters of distilled trichlorobenzene was added into the test tube. The test tube was placed in an oil bath at a temperature of 210° C. to 225° C. such that the tube was immersed just to the level of the trichlorobenzene (about 3 cm) so approximately 10 cm of the tube exposed to air could act as a condenser. The test tube remained in the oil bath at the above temperature for a period of 48 hours and was then removed and cooled to ambient temperature. Because the effluent argon stream showed hydrogen chloride evolution as determined with pH paper, the test tube was placed again in the oil bath at a temperature of 220° C. After 24 hours in the oil bath, no hydrogen chloride evolution was detected in the effluent argon stream. The test tube was removed from the oil bath and cooled to ambient temperature. The reaction mixture was diluted with 4 milliliters of methanol, filtered and the collected solid washed with pyridine and then methanol. The collected solid product fraction was dried in a vaxuum oven at a temperature of 60° C. to give 0.21 grams (81 percent of theoretical) of a polyester polymeric composition containing, as monomeric components, the bisphenol monomer prepared in accordance with the procedure described in Example 1 and the isophthalate moiety.

EXAMPLE 4

Preparation of Polyester Polymeric Composition

The preparation of the polyester polymeric composition in Example 3 was repeated with the exception that the following ingredients were used in the following amounts:

Bisphenol Monomer (prepared according to Example 1 ): 0.501 millimoles
Isophthaloyl Chloride: 0.255 millimoles
Terephthaloyl Chloride: 0.250 millimoles
Trichlorobenzene: 5 milliliters The collected solid product fraction was not extracted as in the previous examples. The yield of the polyester polymeric composition was 87 percent of theoretical.

EXAMPLE 5

Preparation of Polyester Polymeric Composition

The preparation of the polyester polymeric composition in Example 3 was repeated at a reaction temperature of 155° C.–160° C. with the exception that the following ingredients were used in the following amounts:

Bisphenol Monomer (prepared according to Example 1 ): 0.499 millimoles
Isophthaloyl Chloride: 0.507 millimoles
N,N-dimethylacetamide: 6.0 milliliters The collected solid product fraction was not extracted as in the previous examples. The yield of the polyester polymeric composition was 72 percent of theoretical.

EXAMPLE 6

Preparation of Polyester Polymeric Composition

The preparation of the polyester polymeric composition in Example 3 was repeated with the exception that the following ingredients were used in the following amounts:

Bisphenol Monomer (prepared according to Example 1 ): 0.499 millimoles
Sebacoyl Chloride (Aldrich, distilled ): 0.499 millimoles
Trichlorobenzene: 6 milliliters The collected solid product fraction was extracted with pyridine. The yield of the polyester polymeric composition was 90 percent of theoretical.

EXAMPLE 7

Preparation of Polycarbonate Polymeric Composition

Into a 50 milliliter reaction flask equipped with a magnetic stirrer, thermometer and serum cap with two syringe needles for nitrogen inlet and phosgene inlet was added 0.20 grams (0.51 millimoles) of the bisphenol monomer prepared in accordance with the procedure described in Example 1 and 30 milliliters of dry pyridine (stored over molecular sieves). The resulting solution was flushed with nitrogen and thereafter heated to a temperature of 80° C. and then cooled to temperature of 40° C. Phosgene was slowly added as a gas entering the reaction flask through the syringe needle placed well above the pyridine solution. A trap between the reaction flask and the phosgene supply (tank) was used with together with a sodium hydroxide/methanol trap to neutralize the phosgene exiting from the reaction. Shortly after the addition of phosgene into the reaction flask, a solid material formed on the surface of the pyridine. The reaction mixture was swirled periodically and the phosgene flow interrupted occasionally with a nitrogen purge. The reaction mixture was then cooled to ambient temperature and purged with nitrogen overnight. The reaction was quenched with methanol, diluted with water, filtered and the collected solid was thereafter stirred with pyridine and collected by filtration. The collected solid product fraction was dried in a vacuum oven at a temperature of 60° C. to give 0.22 grams (~100 percent of theoretical) of a polycarbonate polymeric composition containing, as monomeric components, the bisphenol monomer prepared in accordance with the procedure described in Example 1 and the carbonyl moiety.

EXAMPLE 8

Preparation of Polysulfone Polymeric Composition

Into a 50 milliliter reaction flask equipped with a side arm fitted with a serum cap and syringe needle for argon inlet and a 5 cm by 1 cm diameter column of freshly dried molecular sieves connected to a condenser was added 392.5 milligrams (1.005 millimoles) of the bisphenol monomer prepared in accordance with the procedure described in Example 1, 93.4 milligrams (0.5016 millimoles) of 4,4'-biphenol (Bayer), 433.4 milligrams (1.509 millimoles) of 4,4'-dichlorodiphenyl sulfone commercially available from Union Carbide Corporation and 0.62 grams (4.5 millimoles) of ground, anhydrous potassium carbonate and 20 milliliters of N,N'-dimethylacetamide (stored over dried molecular sieves). The resulting reaction mixture was purged with argon for 15 minutes and then heated in an oil bath. Four milliliters of xylene were added to the column containing the molecular sieves. At an oil bath temperature of 150° C., the reaction mixture was a bright red-orange color and all of the organic components had dissolved in solution. The argon flow was reduced to a slow purge and the reaction mixture was further heated at an oil bath temperature of 170° C. for 24 hours (after 16 an additional 5 milliliters of N,N-dimethylacetamide was added to the reaction flask) and then cooled to ambient temperature. The reaction mixture (red-brown solid and solution) was then transferred with N,N-dimethylacetamide to a glass beaker and stirred with a small amount of oxalic acid which resulted in the red-brown solid and solution turning to a lighter yellow color. The solid and solution were then diluted with an equal volume of water, filtered, and the collected solid as washed with isopropanol and dried in a vacuum oven at a temperature of 60° C. The dried collected solid was then stirred twice with pyridine (100 milliliters each time) to remove any unreacted monomer, filtered and the collected solid product fraction was washed with isopropanol and dried in a vacuum oven at a temperature of 60° C. to give 0.65 grams (80 percent of theoretical) of a polysulfone polymeric composition containing, as monomeric components, the visphenol monomer prepared in accordance with the procedure described in Example 1, 4,4'-biphenol and the residuum of 4,4'-dichlorodiphenyl sulfone.

EXAMPLE 9

Preparation of Polysulfone Polymeric Composition

The preparation of the polysulfone polymeric composition in Example 8 was repeated with the exception that the following ingredients were used in the following amounts:
  Bisphenol Monomer (prepared 0.501 millimoles according to Example 1):
  4,4'Biphenol: 0.499 millimoles
  4,4'Dichlorodiphenyl sulfone: 1.00 millimoles
  N,N-Dimethylacetamide: 5 milliliters In addition, methyl chloride was sparged through the reaction mixture after polymerization was complete and before isolation of the polymeric product to end cap the polymeric composition. The collected solid product fraction was extracted with pyridine. The yield of the polysulfone polymeric composition was 85 percent of theoretical.

EXAMPLE 10

Preparation of Polysulfone Polymeric Composition

The preparation of the polysulfone polymeric composition in Example 8 was repeated with the exception that the following ingredients were used in the following amounts:
  Bisphenol Monomer (prepared 100 millimoles according to Example 1):
  Bisphenol A (commercially available from Dow Chemical Company): 1.27 millimoles
  4,4'Dichlorodiphenyl Sulfone: 2.27 millimoles
  N,N-Dimethylacetamide: 7 milliliters The collected solid product fraction was extracted with both chloroform and pyridine. The yield of the polysulfone polymeric composition was 92 percent of theoretical.

EXAMPLE 11

Preparation of Polysulfone Polymeric Composition

The preparation of the polysulfone polymeric composition in Example 8 was repeated with the exception that the following ingredients were used in the following amounts:
  Bisphenol Monomer (prepared according to Example 1): 1.00 millimoles
  Bisphenol A (commercially available from Dow Chemical Company): 1.00 millimoles
  4,4-Dichlorodiphenyl Sulfone: 2.00 millimoles
  N,N-Dimethylacetamide: 7 milliliters The collected solid product fraction was extracted with both chlo/roform and pyridine. The yield of the polysulfone polymeric composition was 63 percent of theoretical.

EXAMPLE 12

Preparation of Polysulfone Polymeric Composition

The preparation of the polysulfone polymeric composition in Example 8 was repeated with the exception that the following ingredients were used in the following amounts:
  Bisphenol Monomer (prepared according to Example 1): 0.499 millimoles
  4,4'Dichlorodiphenyl Sulforn: 0.498 millimoles
  N,N-Dimethylacetamide: 5 milliliters The collected solid product fraction was extracted as in the previous examples. The yield of the polysulfone polymeric composition was 83 percent of theoretical.

EXAMPLE 13

Preparation of Polysulfone Polymeric Composition

The preparation of the polysulfone polymeric composition in Example 8 was repeated with the exception that the following ingredients were used in the following amounts:
  Bisphenol Monomer (prepared according to Example 1): 2.502 millimoles
  4,4'Dichlorodiphenyl Sulfone: 2.506 millimoles
  N,N-Dimethylacetamide: 25 milliliters The collected solid product fraction was extracted with pyridine.

EXAMPLES 14 THROUGH 24 AND COMPARATIVE EXAMPLE A

Microscopic Examination of Polymeric Compositions

A common method used to detect liquid crystal behavior is to observe a melt or solution of the polymeric composition with a microscope under cross-polarized light. An isotropic liquid (random arrangement and three degrees of translational freedom) will show a uniformly dark field under microscopic examination. A crystalline substance may generally show bright birefringent patterns in a spectrum of colors under such microscopic examination. Liquid crystal phases will often show similar birefringent patterns but with two important distinctions: (1) the birefringent patterns are mobile, i.e., pushing on the sample shows obvious flow and alterations in the patterns; and (2) the bright areas are interspersed with or separated by dark "lines" or "threads" which are mobile and these "lines" or "threads" are often referred to as texture.

Certain of the polymeric compositions prepared in the Examples hereinabove and identified in Table A below were examined on a hot-stage microscope equipped with argon purge for liquid crystal behavior by heating the polymeric composition sample between the microscope glass cover slips. In addition, a comparative polymeric composition commercially designated as X7H (Eastman Kodak Company) was also examined on a hot-stage microscope for liquid crystal behavior. The X7H polymeric composition is essentially a copolymer of a p-hydroxybenzoic acid with poly (ethylene terephthalate) which is processable in the melt and is known to exhibit liquid crystal behavior. See F.M. Silver and W.B. Black, J. Poly. Sci., Poly Chem. Ed., 17,3543 (1979). The results of the microscopic examination of the polymeric compositions are given in Table A.

The mobile liquid crystal phase of X7H was easily observed under microscopic examination; in fact, it was determined that X7H consisted of both an isotropic phase and a liquid crystal phase in the melt (335° C.-970° C.). The polyester examined in Example 14 and the polycarbonate examined in Example 15 both melted at about 360° C.-370° C. and showed highly colored (bright rainbow colors), nematic textured mobile melts under microscopic examination. Other polymeric compositions in Table A also showed evidence of liquid crystal behavior (see Examples 16-20). However, unlike the X7H, the polyester examined in Example 14 and the polycarbonate examined in Example 15, the remaining polymeric compositions in Table A melted at much higher temperatures and, under slow heating conditions, polymer degradation was too fast causing cross-linking and thermal decomposition of these polymeric compositions. It was necessary to preheat the hot stage on the microscope to a selected temperature, quickly place the sample on the hot stage, press the cover slips together, remove the melted sample quickly after flow was achieved, and cool the sample. Microscopic examination was done on these solid pressed samples so mobile phases could not be observed. However, nematic texture similarities and characteristic birefringent patterns weere observed whivh were also observed for X7H.

It is noted that the polysulfone polymeric compositions incorporating visphenol A and 4,4'biphenol in addition to the rigid monomeric compositions, as illustrated in Examples 21 through 24, generally showed little or no evidence for liquid crystal properties. Example 21 in which the polysulfone polymeric composition had a mole ratio of rigid monomeric composition to 4,4'biphenol of about 2, did exhibit some nematic texture indicating a degree of liquid crystal properties. However, in Examples 22 to 24 in which the polysulfone polymeric composition had a mole ratio of rigid monomeric composition to either 4,4'biphenol or bisphenol A of less than or about equal to one, there was no evidence for liquid crystal properties. The polysulfone polymeric compositions examined in Examples 18 and 19 (4,4'biphenol and bisphenol A not included therein) showed fine nematic texture characteristic of liquid crystal behavior. These examples demonstrate

TABLE A
MICROSCOPIC EXAMINATION OF POLYMERIC COMPOSITIONS

| Example | Polymeric Composition Identification | Melt Temperature (°C.) | Microscopic Appearance |
|---|---|---|---|
| A | X7H | 335-370 | Mobile; fine nematic texture; isotropic phase present also. |
| 14 | Polyester prepared in Example 5 | 360-370 | Mobile; brilliant birefringent; nematic texture. |
| 15 | Polycarbonate prepared in Example 7 | 370 | Mobile; brilliant birefringent; nematic texture. |
| 16 | Polyester prepared in Example 3 | 500-510* | Fine nematic texture. |
| 17 | Polyester prepared in Example 4 | 550-560* | Fine nematic texture. |
| 18 | Polysulfone prepared in Example 12 | 465* | Some fine nematic texture; isotropic phase present also. |
| 19 | Polysulfone prepared in Example 13 | 464-471* | Fine nematic texture. |
| 20 | Polyester prepared in Example 6 | 410-465* | Very fine nematic texture; some isotropic phase present also. |
| 21 | Polysulfone prepared in Example 8 | 455-470* | Mostly isotropic phase with a few small nematic textured areas. |
| 22 | Polysulfone prepared in Example 11 | 468* | No texture. |
| 23 | Polysulfone prepared in Example 10 | 468* | Some birefringent areas but no texture; isotropic phase present. |
| 24 | Polysulfone prepared in Example 9 | 455-475* | Isotropic phase only; no texture. |

*Sample was placed on preheated hot-stage, melted, removed and cooled. Microscopic examination was on solid sample so mobile phases could not be observed.

that the liquid crystal behavior observed in Examples 14 through 20 and partially in Example 21 is directly related to the presence of the rigid monomeric composition in the polymeric compositions. When excessive proportions of normal bisphenols having non-rigid or flexible structure, e.g., bisphenol A, and/or low aspect ratios, e.g., 4,4′biphenol having an aspect ratio of about 2.0, are incorporated into the polymeric composition structure, thereby reducing the proportion the rigid monomeric composition incorporated into the polymeric composition, the resulting polymeric compositions may not necessarily exhibit liquid crystal properties.

I claim:

1. A substantially linear monomeric composition of the formula:

$$E^1-R^1(R^2{}_mR^3{}_n)R^4-E^2$$

wherein
$R^1$ and $R^4$ are individually a substituted or unsubstituted aromatic or heteroaromatic group having from 5 to about 20 carbon atoms, $R^2$ is a substituted or unsubstituted aromatic, heteroaromatic or cycloaliphatic group having from 5 to 20 carbon atoms,
$R^3$ is selected from the group consisting of:

[structures: >C=C< with H,H; >C=N with H; >C=P with H; >C=Si< with H; >C=C< with CH3,CH3; >C=C< with CN,H; -C(F)=C(F)-; and -C(F)=C(H)-], $E^1$ and $E^2$ are individually a hydroxyl radical, $-NH_2$, $-\overset{H}{\underset{}{N}}-\overset{O}{\underset{}{C}}-CH_3$, or an acyl radical having the formula:

$$R^7-\overset{O}{\underset{}{C}}-Z-$$

wherein $R^7$ is hydrogen, hydroxyl, halogen or a substituted or unsubstituted alkyl, aryl or arylalkyl group having from 1 to about 20 carbon atoms and Z is oxygen or nitrogen, and wherein m has a value of at least 2 and n has a value of at least 1 such that the aspect ratio of the composition is from about 3.5 to about to about 7.0 and, when m and/or n are values of 2 or greater, $R^2$ and $R^3$ individually can be the same or different groups, and the $R^2$ and $R^3$ group(s) can be arranged in any order provided two or more $R^3$ groups are not directly connected to each other with a chemical bond.

2. A substantially linear monomeric composition as defined in claim 1 wherein $R^1$ and $R^4$ are individually selected from the group consisting of

[phenyl and biphenyl structures]

3. A substantially linear monomeric composition as defined in claim 2 where $R^2$ is selected from the group consisting of

[phenyl, biphenyl, pyromellitimide bis-N, and cyclohexyl structures]

4. A substantially linear monomeric composition as defined in claim 1 wherein m has a value of from 2 to about 4.

5. A substantially linear monomeric composition as defined in claim 4 wherein n has a value of from 1 to about 4.

6. A substantially linear monomeric composition as defined in claim 5 wherein the aspect ratio is from about 3.5 to about 5.5.

7. A substantially linear monomeric composition having the formula

[HO-phenyl-CH=CH-phenyl-phenyl-CH=CH-phenyl-OH]

or a carboxylic acid ester thereof having the formula

[CH3CO-O-phenyl-CH=CH-phenyl-phenyl-CH=CH-phenyl-O-OCCH3]

8. A substantially linear monomeric composition having the formula

[HO-phenyl-phenyl-CH=CH-phenyl-phenyl-OH]

or a carboxylic acid ester thereof having the formula
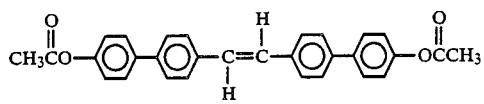
9. A substantially linear monomeric composition as defined in claim 1 wherein
$$E^1-R^1-(-R^2{}_m-R^3{}_n-)-R^4-E^2$$
is selected from the following:
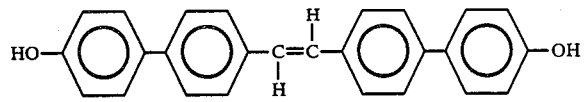
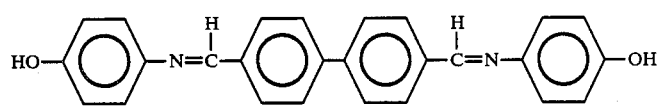
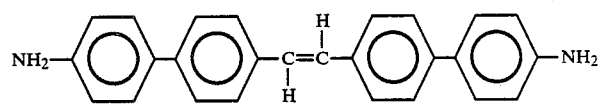
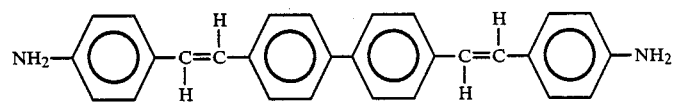
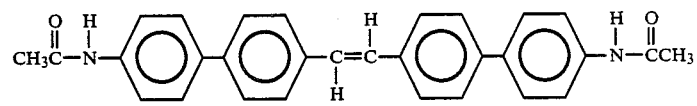
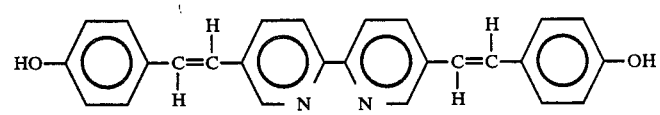
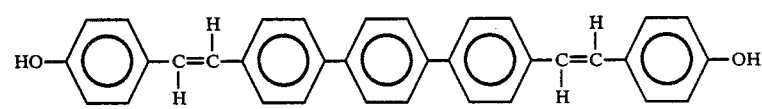
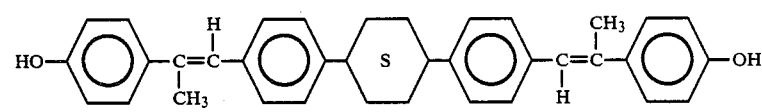

-continued
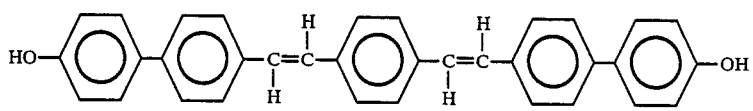
10. A substantially linear monomeric composition as difined in claim 1 wherein
$$E^1-R^1-(-R^2{}_m-R^3{}_n)-R^4-E^2$$
is selected from the following:
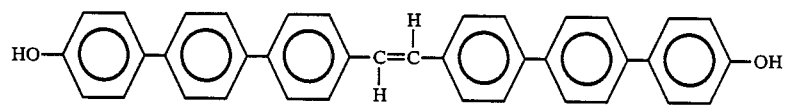
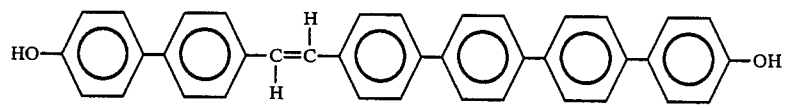
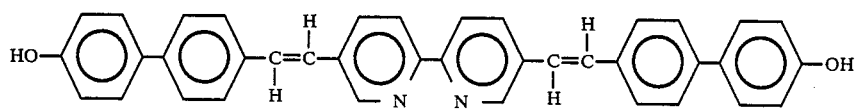
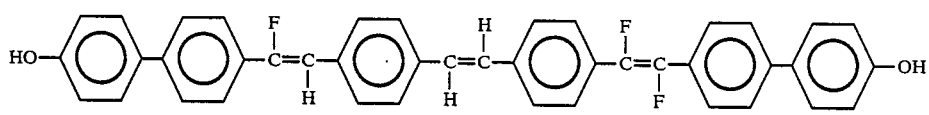
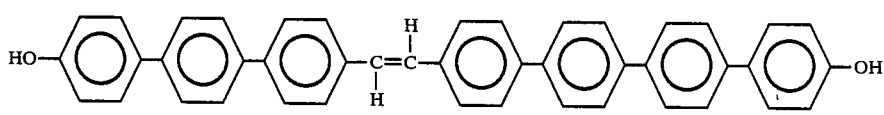
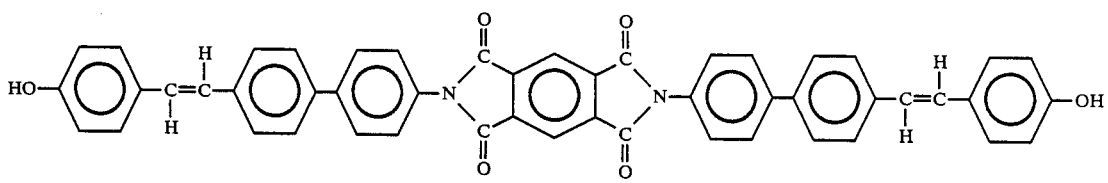
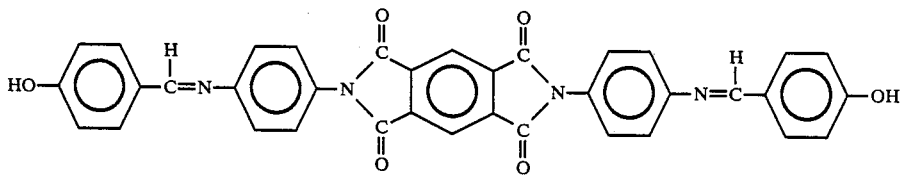
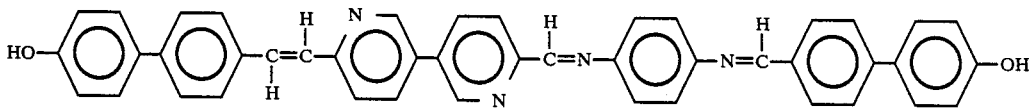
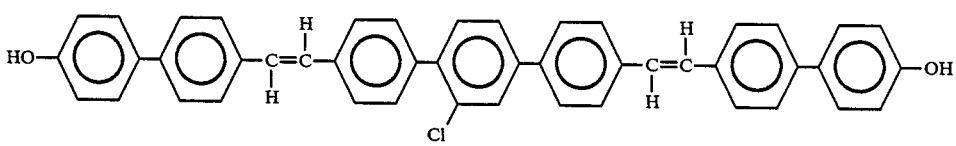

-continued

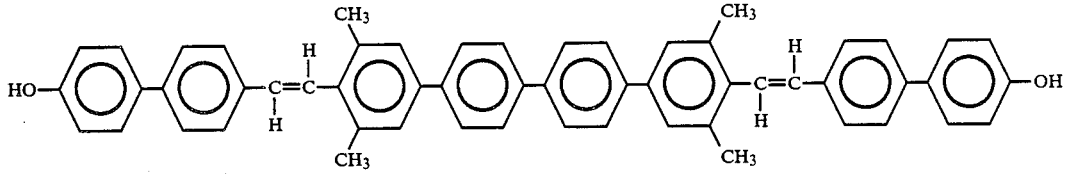

11. A process for preparing a substantially linear monomeric composition which comprises:
(1) preparing a reaction mixture comprising at least one difunctional reactant selected from the group consisting of
(a) acetic anhydride and
(b) substituted or unsubstituted aromatic, hereroaromatic or cycloaliphatic group having from 5 to 20 carbon atoms which appear individually or are joined by:

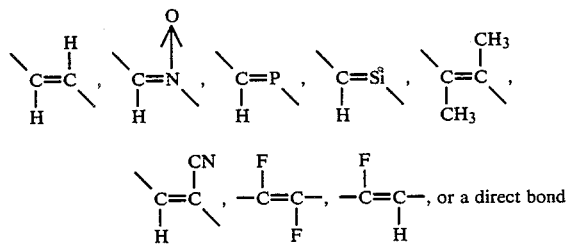

and, in at least stoichiometric amounts, at least one monofunctional reactant selected from the group consisting of p-cresol, para methyl phenyl acetate, N-bromosuccinimide, triphenylphoshine, triphenylphoshine salt of para bromomethylphenyl acetate, triphenylphosphine salt of para bromobenzyl bromide, p-chlorobenzaldehyde, 4-bromobenzaldehyde, and para-chlorophenyl acetate;
(2) reacting said reactants for a time and at a temperature sufficient to form a product mixture comprising a substantially linear monomeric composition of the formula:

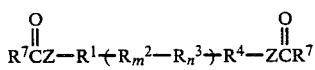

wherein
$R^1$ and $R^4$ are individually a substituted or unsubstituted aromatic or heteroaromatic group having from 5 to about 20 carbon atoms,
$R^2$ is a substituted or unsubstituted aromatic, heteroaromatic or cycloaliphatic group having from 5 to about 20 carbon atoms,
$R^3$ is selected from the group consisting of

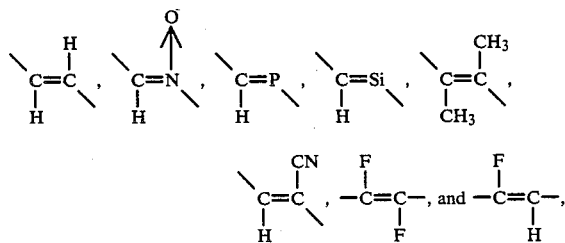

$R^7$ is hydrogen, hydroxyl, halogen or a substituted or unsubstituted alkyl, aryl or arylalky group having from 1 to about 20 carbon atoms and Z is oxygen or nitrogen, and wherein m has a value of at least 2 and n has a value of at least 1 such that the aspect ratio of the composition is from about 3.5 to about 7.0 and, when m and/or n are values of 2 or greater, $R^2$ and $R^3$ individually can be the same or different groups, and the $R^2$ and $R^3$ group(s) be arranged in any order provided two or more $R^3$ groups are not directly connected to each other with a chemical bond; and
(3) optionally reacting the product mixture comprising the substantially linear monomeric composition prepared in (2) with a protic solvent in the presence of an acidic or basic catalyst for a time and at a temperature sufficient to form a product mixture comprising a substantially linear monomeric compositin of the formula:

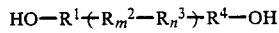

or the diamino analog thereof, wherein $R^1$, $R^2R^3$, $R^4$, m, and n are as defined hereinbefore.

12. A process for preparing a substantially linear monomeric composition as defined in claim 11 wherein the monofunctional reactant (s) are selected from the group consisting of para-chlorophenyl acetate, and the triphenylphosphine salt of para-bromomethylphenyl acetate.

13. A process for preparing a substantially linear monomeric composition as defined in claim 12 wherein the difunctional reactant (s) are selected from the group consisting of 4,4'biphenyldialdehyde and 4,4'dibromostilbene.

14. A process for preparing a substantially linear monomeric composition as defined in claim 13 wherein step (2) comprises reacting said reactants at a temperature of from about 25° C. to about 350° C. from about 1 hour to about 300 hours.

15. A process for preparing a substantially linear monomeric composition as defined in claim 14 wherein step (3) comprises reacting said reactants at a temperature of from about 25° C. to about 350° C. for a period of from about 1 hour to about 72 hours.

16. A process for preparing a substantially linear monomeric composition as defined in claim 15 wherein the protic solvent in (3) is selected from absolute ethanol and aqueous dioxane.

17. A process for preparing a substantially linear monomeric composition as defined in claim 16 wherein the acidic or basic catalyst in (3) is selected from sulfuric acid, paratoluene sulfonic acid and the alkali metal hydroxides, alkoxides and carbonates.

18. A process for preparing a substantially linear monomeric composition as defined in claim 17 wherein the monofunctional reactant in (1) is the triphenylphosphine salt of para-bromomethylphenyl acetate, the difunctional reactant in (1) is 4,4'biphenyldialdehyde, the substantially linear monomeric composition in (2) has the formula

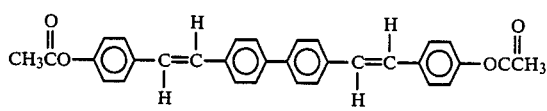

and the substantially linear monomeric composition in (3) has the formula

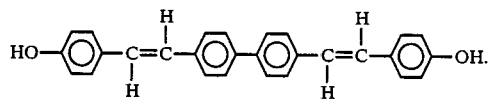

19. A process for preparing a substantially linear monomeric composition as defined in claim 17 wherein the monofunctional reactant in (1) is para-chlorophenyl acetate, the difunctional reactant in (1) is 4,4′dibromostilbene, the substantially linear monomeric composition in (2) has the formula

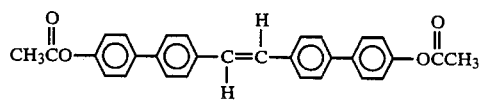

and the substantially linear monomeric composition in (3) has the formula

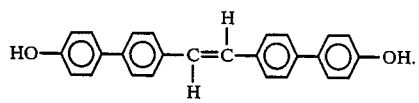

20. A process for preparing a polymeric composition comprising polymerizing one or more difunctional monomers with a substantially linear monomeric composition of the formula:

$$E^1-R^1-(R_m{}^2-R_n{}^3)-R^4-E^2$$

wherein
$R^1$ and $R^4$ are individually a substituted or unsubstituted aromatic or heteroaromatic group having from 5 to about 20 carbon atoms,
$R^2$ is a substituted or unsubstituted aromatic, heteroaromatic or cycloaliphatic group having from 5 to about 20 carbon atoms,
$R^3$ is selected from the group consisting of:

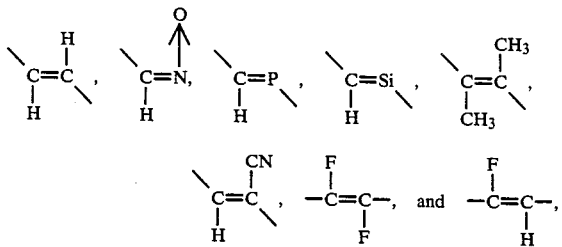

$E^1$ and $E^2$ are individually a hydroxyl radical,

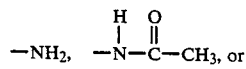

an acyl radical having the formula:

wherein $R^7$ is hydrogen, hydroxyl, halogen or a substituted or unsubstituted alkylm aryl or arylalky group having from 1 to about 2 carbon atoms and Z is oxygen or nitrogen, and wherein m has a value of at least 2 and n has a value of at least 1 such that theaspect ratio of the composition is from about 3.5 to about 7.0 and, when m and/or n are values of 2 or greater, $R^2$ and $R^3$ individually can be the same or different groups, and the $R^2$ and $R^3$ groups are not directly connected to each other with a chemical bond, in the presence of an aprotic solvent at a temperature of from about ambient to about 400° C. for a period of from about 1 hour to about 96 hours.

21. A process for preparing a polymeric composition as defined in claim 20 wherein the aprotic solvent is N, -dimethylacetamide.

22. A process for preparing a polymeric composition as defined in claim 20 wherein the temperature is greater than about 100° C.

23. A process for preparing a polymeric composition as defined in claim 20 wherein the difunctional monomer (s) are selected from the group consisting of
(1) a difunctional monomer having the formula

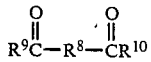

wherein $R^8$ is a substituted or unsubstituted alkyl group having from 1 to about 20 carbon atoms or a substituted or unsubstituted aromatic, heteroaromatic or cycloaliphatic group having from 5 to about 20 carbon atoms and $R^9$ and $R^{10}$ are individually halogen or $-OR^{11}$ wherein $R^{11}$ is hydrogen or a substituted or unsubstituted alkyl, aryl or arylalkyl group having from 1 to about 20 carbon atoms, with the proviso that when $R^9$ and/or $R^{10}$ are halogen or when $R^9$ and/or $R^{10}$ are $-OR^{11}$ wherein $R^{11}$ is not hydrogen, then $E^1$ and/or $E^2$ in the substantially linear monomeric composition are a hydroxyl radical or an amino radical;
(2) a difunctional monmer having the formula

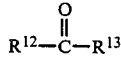

wherein $R^{12}$ and $R^{13}$ are individually halogen or $-OR^{14}$ in which $R^{14}$ is a substituted or unsubstituted alkyl, aryl or arylalkyl group having from 1 to about 20 carbon atoms;
(3) a difunctional monomer having the formula

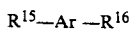

wherein Ar is the residuum of a benzenoid compound having at least one electronm withdrawing group in one or more of the positions ortho or para to $R^{15}$ and $R^{16}$ and wherein $R^{15}$ and $R^{16}$ are individually halogen, $-NO_2$, $-OSOR^{17}$ or $-OSO_2R^{18}$ in which $R^{17}$ and $R^{18}$ are a substituted or unsubstituted hydrocarbon group; and
(4) a difunctional monomer having the formula $$O=C=N-R^{19}-N=C=O$$

wherein $R^{19}$ is a substituted or unsubstituted alkyl, aryl or arylalkyl group having from 1 to about 20 carbon atoms.

24. A process for preparing a polymeric composition as defined in claim 23 wherein the difunctional monomer (s) are selected from the group consisting of sebacoyl chlorid, isophthaloyl chloride, terephthaloyl chloride, mictures of isophthaloyl chloride and terephthaloyl chloride, carbonyl chloride (phosgene), 4,4′-dichlorodiphenyl sulfone and 2,4-or 2,6-tolylene diisocyanate.

25. A process for preparing a polymeric composition as defined in claim 20 wherein the substantially linear monomeric composition is selected from the group consisting of the following:

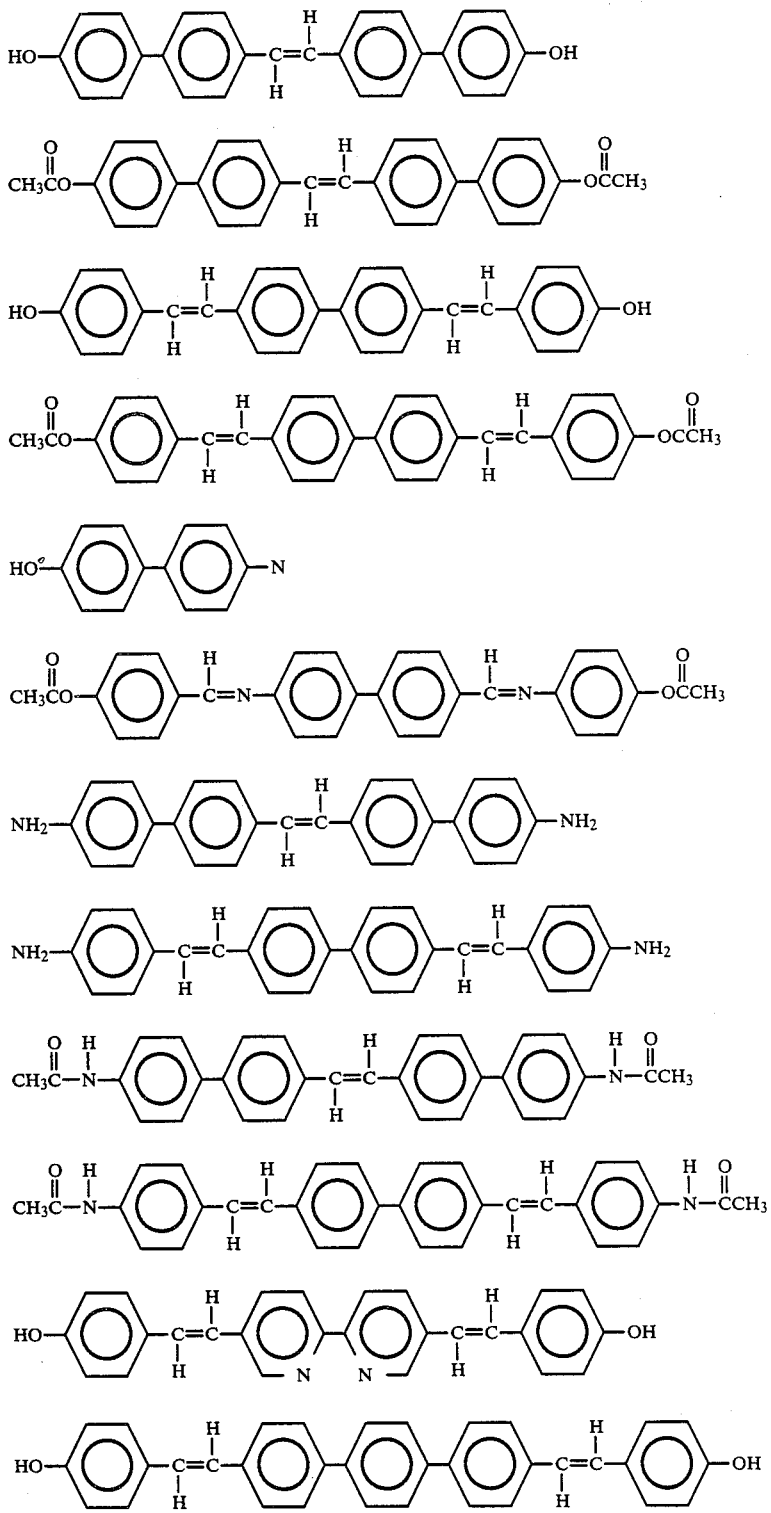

-continued
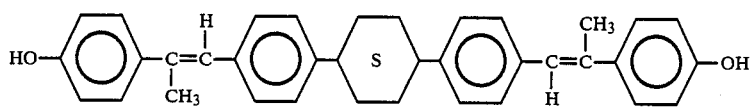
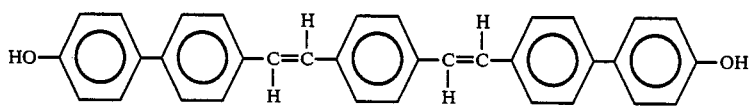
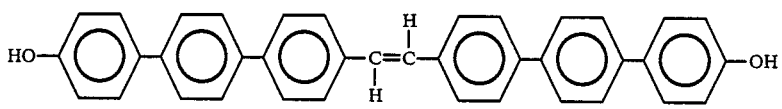
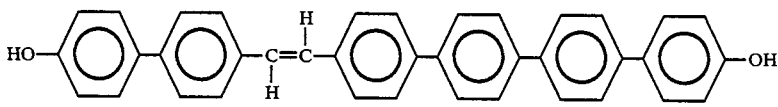
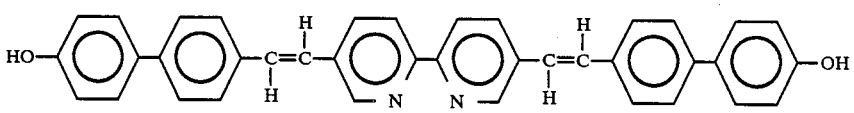
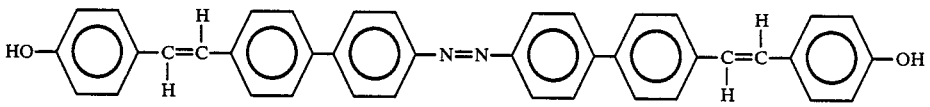
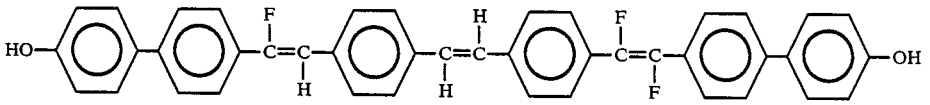
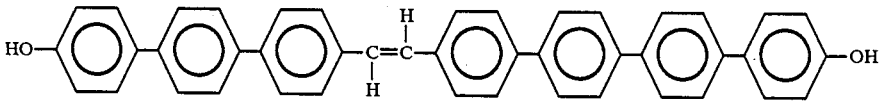
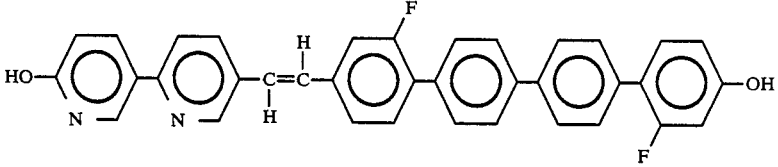
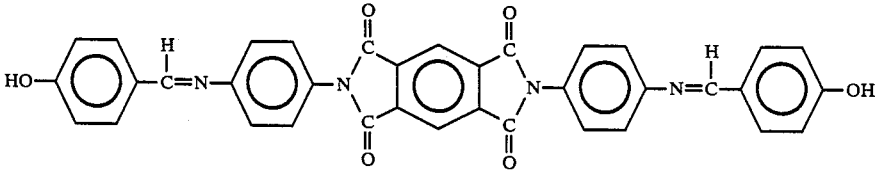
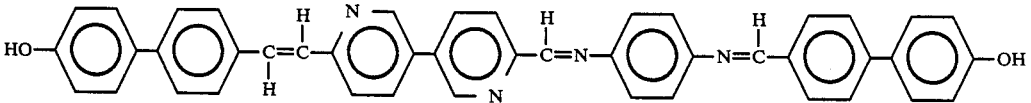
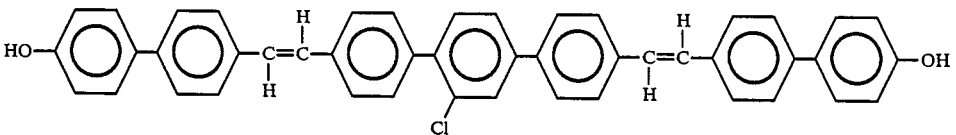

-continued

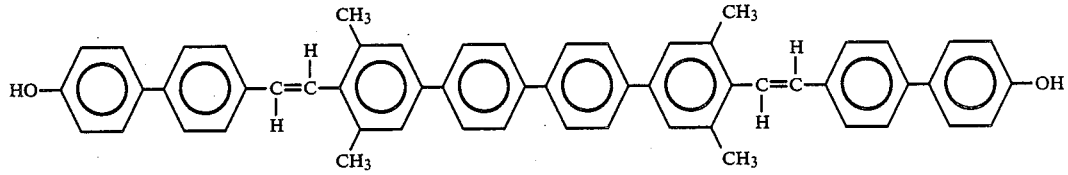

26. A process for preparing a polymeric composition as defined in claim 20 wherein sebacoyl chloride is polymerized with a substantially linear monomeric composition of the formula

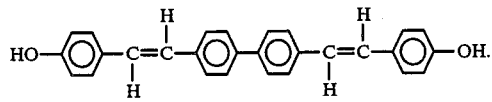

27. A process for preparing a polymeric composition as defined in claim 20 wherein isophthaloyl chloride is polymerized with a substantially linear monomeric composition of the formula

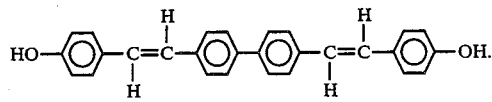

28. A process for preparing a polymeric composition as defined in claim 20 wherein a mixture of isophthaloyl chloride and terephthaloyl chloride is polymerized with a substantially linear monomeric composition of the formula

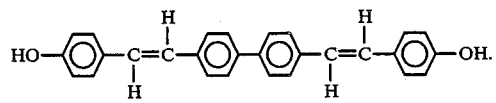

29. A process for preparing a polymeric composition as defined in claim 20 wherein carbonyl chloride (phosgene) is polymerized with a substantially linear monomeric compositon of the formula

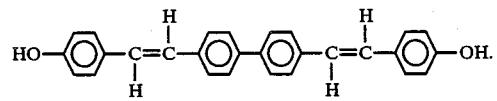

30. A process for preparing a polymeric compositon as defined in claim 20 wherein 4,4'dichlorodiphenyl sulfone is polymerized with a substantially linear monomeric composition of the formula

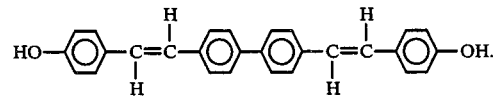

31. A process for preparing a polymeric composition as defined in claim 20 wherein 4,4'dichlorodiphenyl sulfone is polymerized with 2,2-(4-hydroxyphenyl) propane and a substantially linear monomeric composition of the formula

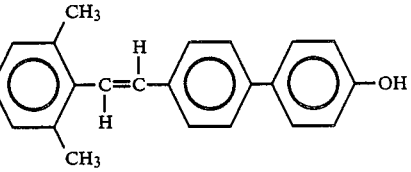

32. A process for preparing a polymeric composition as defined in claim 20 wherein 4,4'dichlorodiphenyl sulfone is polymerized with 4,4'biphenol and a substantially linear monomeric composition of the formula

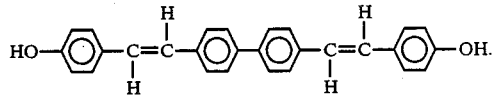

33. A process for preparing a polymeric composition as defined in claim 20 further comprising polymerizing a dihydric phenol with the substantially linear monomeric composition.

34. A process for preparing a polymeric composition as difined in claim 33 wherein the dihydric phenol is seelected from the group consisting of 4,4'biphenol hydroquinone and 2,2-bis-(4hydroxyphenyl) propane.

35. A process for preparing a polymeric composition as defined in claim 20 wherein the polymeric composition has liquid crystal properties.

36. The polymeric composition prepared according to the process of claim 20.

37. The polymeric composition prepared according to the process of claim 20 having liquid crystal properties.

38. The polymeric composition prepared according to the process of claim 23.

39. The polymeric composition prepared according to the process of claim 26.

40. The polymeric composition prepared according to the process of claim 27.

41. The polymeric composition prepared according to the process of claim 28.

42. The polymeric composition prepared according to the process of claim 29.

43. The polymeric composition prepared according to the process of claim 30.

44. The polymeric composition prepared according to the process of claim 31.

45. The polymeric composition prepared according to the process of claim 32.

46. A substantially linear polymeric composition having repeating units of the formula:

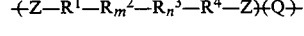

wherein

R$^1$ and R$^4$ are individually a substituted or unsubstituted aromatic or heteroaromatic group having from 5 to about 20 carbon atoms, $R^2$ is a substituted or unsubtituted aromatic, heteroaromatic or cycloaliphatic group having from 5 to about 20 carbon atoms, $R^3$ is selected from the group consisting of:

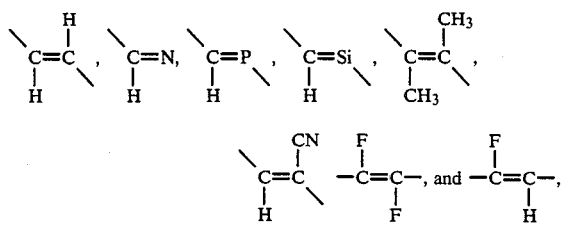

Z is oxygen or nitrogen, and
wherein
m has a value of at least 2 and n has a value of at least 1 such that the aspect ratio of the composition is from about 3.5 to about 7.0 and, when m and/or n are values of 2 or greater, $R^2$ and $R^3$ individually can be the same or different groups, and the $R^2$ and $R^3$ group(s) can be arranged in any order provided two or more $R^3$ groups are not directly connected to each other with a chemical bond; and Q is the residuum of a difunctional monomer selected from the following:

(1) a difunctional monomer having the formula:

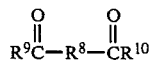

wherein
$R^8$ is a substituted or unsubstituted alkyl group having from 1 to about 20 carbon atoms or a substituted or unsubstituted aromatic, heteroaromatic or cycloaliphatic group having from 5 to about 20 carbon atoms and $R^9$ and $R^{10}$ are individually halogen or $-OR^{11}$ wherein $R^{11}$ is hydrogen or a substituted or unsubstitued alkyl, aryl or arylalkyl group having from 1 to about 20 carbon atoms, with the proviso that when $R^9$ and/or $R^{10}$ are halogen or when $R^9$ and/or $R^{10}$ are $-OR^{11}$ wherein $R^{11}$ is not hydrogen, then $E^1$ and/or $E^2$ in the substantially linear monomeric composition are a hydroxyl radical or an amino radical;

(2) a difunctional monomer having the formula

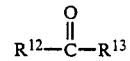

wherein $R^{12}$ and $R^{13}$ are individually halogen or $-OR^{14}$ in which $R^{14}$ is a substituted or unsubstituted alkyl, aryl or arylalkyl group having from 1 to about 20 carbon atoms;

(3) a difunctional monomer having the formula

wherein Ar is the residuum of a benzenoid compound having at least one electron withdrawing group in one or more of the positions ortho or para to $R^{15}$ and $R^{16}$ and wherein $R^{15}$ and $R^{16}$ are individually halogen, $-NO_2$, $-OSOR^{17}$ or $-OSO_2 R^{18}$ in which $R^{17}$ and $R^{18}$ are a substituted or unsubstituted hydocarbon group; and (4) a difunctional monomer having the formula

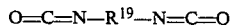

wherein $R^{19}$ is a substituted or unsubstituted alkyl, aryl or arylalkyl having from 1 to about 20 carbon atoms.

* * * * *

UNITED STATES PATENT OFFICE
CERTIFICATE OF CORRECTION

Patent No. 4,841,009  Dated June 20, 1989

Inventor(s) Donald Ross Kelsey

It is certified that error appears in the above-identified patent and that said Letters Patent is hereby corrected as shown below:

| Column | Line | |
|---|---|---|
| 1 | 37 | "of a " should read —of a helical nature.— |
| 13 | 1st formula | "  " should read -- — (formula should be omitted) |
| 38 | 56-7 | "sodium ethanol" should read —ethanol— |
| 38 | 64 | "0.6" should read —0.16— |
| 41 | 47 | "visphenol" should read —bisphenol— |
| 41 | 59-60 | "(prepared 0.501 millimoles according to Example 1):" should read --(prepared according to Example 1): 0.501 millimoles— |
| 42 | 11-12 | "(prepared 100 millimoles according to Example 1):" should read --(prepared according to Example 1): 100 millimoles— |
| 42 | 36 | "chlo/roform" should read —chloroform— |

UNITED STATES PATENT OFFICE
CERTIFICATE OF CORRECTION

Patent No. 4,841,009  Dated June 20, 1989

Inventor(s) Donald Ross Kelsey

It is certified that error appears in the above-identified patent and that said Letters Patent is hereby corrected as shown below:

Column   Line 21-22 "
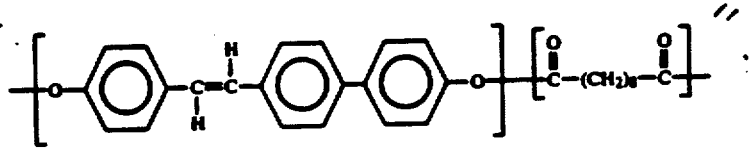
"

should read --

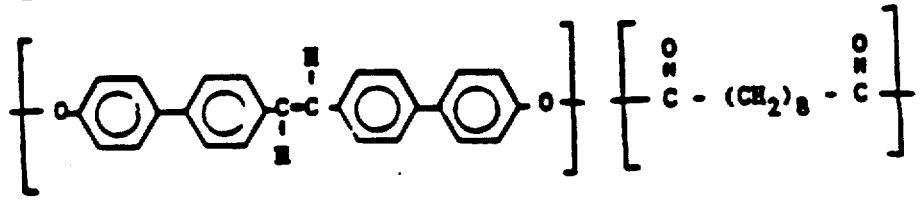

31 "
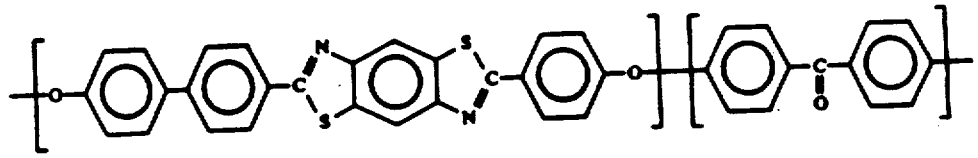
"

should be deleted

UNITED STATES PATENT OFFICE
CERTIFICATE OF CORRECTION

Patent No. 4,841,009

Dated June 20, 1989

Inventor(s) Donald Ross Kelsey

It is certified that error appears in the above-identified patent and that said Letters Patent is hereby corrected as shown below:

| Column | Line | |
|---|---|---|
| 42 | 50 | "4,4'Dichlorodiphenyl Sulforn" should read --4,4'-Dichlorodiphenyl Sulfone-- |
| 44 | 25 | "visphenol" should read -- bisphenol -- |
| 54 | 7 | "alkylm aryl or arylalky" should read --alkyl, aryl, or arylalkyl-- |
| 54 | 8 | "2" should read --20-- |
| 47-48 | | Claim 9, after the first formula should be inserted |

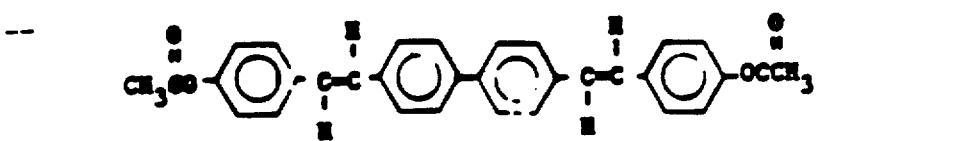

| | | |
|---|---|---|
| 54 | 8 | "2" should read --20-- |
| 54 | 14 | "$R^3$ groups" should read --$R^3$ group(s) can be arranged in any order provided two or more $R^3$ groups-- |

UNITED STATES PATENT AND TRADEMARK OFFICE
CERTIFICATE OF CORRECTION

PATENT NO. : 4,841,009

DATED : June 20, 1989

INVENTOR(S) : Donald Ross Kelsey

It is certified that error appears in the above-identified patent and that said Letters Patent is hereby corrected as shown below:

Column   Line 55-56      "  " should be deleted

Signed and Sealed this

Twenty-ninth Day of May, 1990

Attest:

HARRY F. MANBECK, JR.

Attesting Officer   Commissioner of Patents and Trademarks